(12) United States Patent
Slone et al.

(10) Patent No.: US 9,788,956 B2
(45) Date of Patent: Oct. 17, 2017

(54) EXTRA-ARTICULAR IMPLANTABLE MECHANICAL ENERGY ABSORBING ASSEMBLIES HAVING TWO DEFLECTING MEMBERS AND METHODS

(71) Applicant: Moximed, Inc., Hayward, CA (US)

(72) Inventors: Clinton N. Slone, San Francisco, CA (US); Anton G. Clifford, Mountain View, CA (US); Benjamin Toru Mino, Somerville, MA (US); Alan C. Regala, Seattle, WA (US)

(73) Assignee: MOXIMED, INC., Hayward, CA (US)

( * ) Notice: Subject to any disclaimer, the term of this patent is extended or adjusted under 35 U.S.C. 154(b) by 464 days.

(21) Appl. No.: 14/065,190

(22) Filed: Oct. 28, 2013

(65) Prior Publication Data

US 2014/0052266 A1 Feb. 20, 2014

Related U.S. Application Data

(63) Continuation of application No. 12/582,178, filed on Oct. 20, 2009, now Pat. No. 8,679,178.

(51) Int. Cl.
*A61F 2/08* (2006.01)
*A61F 2/38* (2006.01)
*A61B 17/56* (2006.01)

(52) U.S. Cl.
CPC ............ *A61F 2/3886* (2013.01); *A61B 17/56* (2013.01); *A61F 2/0811* (2013.01); *A61F 2/384* (2013.01); *A61B 2017/567* (2013.01); *A61F 2/38* (2013.01); *A61F 2002/0829* (2013.01); *A61F 2002/0864* (2013.01); *A61F 2002/0888* (2013.01)

(58) Field of Classification Search
CPC ....................................... A61F 2/0811
USPC ....................................... 623/13.12
See application file for complete search history.

(56) References Cited

U.S. PATENT DOCUMENTS

| | | |
|---|---|---|
| 2,267,848 A | 12/1941 | Taylor |
| 3,242,922 A | 3/1966 | Thomas |
| 3,648,294 A | 3/1972 | Shahrestani |
| 3,928,872 A | 12/1975 | Johnson |
| 4,100,918 A | 7/1978 | Glancy |
| 4,187,841 A | 2/1980 | Knutson |

(Continued)

OTHER PUBLICATIONS

Supplementary European Search Report for European Patent App. No. 10825425.1 (Jun. 3, 2015).

(Continued)

*Primary Examiner* — David Isabella
*Assistant Examiner* — Christine Nelson
(74) *Attorney, Agent, or Firm* — Adam J. Cermak; Cermak Nakajima & McGowan LLP

(57) ABSTRACT

Implantable assemblies for manipulating energy transferred by members defining an anatomical joint, and methods of implanting and using. The members of the anatomical joint collectively define a path of motion. An assembly includes a first component configured to be attached to a first member of the anatomical joint; a second component configured to be attached to a second member of the anatomical joint; and a joint joining the first and second components. The first component includes a first flex member and the second component includes a second flex member. The first and second flex members are configured to flex to absorb energy transferred by the members of the anatomical joint.

11 Claims, 16 Drawing Sheets

(56) References Cited

U.S. PATENT DOCUMENTS

| | | |
|---|---|---|
| 4,246,660 A | 1/1981 | Wevers |
| 4,308,863 A | 1/1982 | Fischer |
| 4,367,562 A | 1/1983 | Gauthier |
| 4,433,679 A | 2/1984 | Mauldin et al. |
| 4,501,266 A | 2/1985 | McDaniel |
| 4,570,625 A | 2/1986 | Harris et al. |
| 4,576,158 A | 3/1986 | Boland |
| 4,621,627 A | 11/1986 | DeBastiani et al. |
| 4,637,382 A | 1/1987 | Walker et al. |
| 4,696,293 A | 9/1987 | Ciullo |
| 4,873,967 A | 10/1989 | Sutherland |
| 4,988,349 A | 1/1991 | Pennig |
| 5,011,497 A | 4/1991 | Persson et al. |
| 5,019,077 A | 5/1991 | Bastiani et al. |
| 5,026,372 A | 6/1991 | Sturtzkopf et al. |
| 5,041,112 A | 8/1991 | Mingozzi et al. |
| 5,062,916 A | 11/1991 | France et al. |
| 5,103,811 A | 4/1992 | Crupi, Jr. |
| 5,152,280 A | 10/1992 | Danieli |
| 5,375,823 A | 12/1994 | Navas et al. |
| 5,405,347 A | 4/1995 | Lee et al. |
| 5,578,038 A | 11/1996 | Slocum |
| 5,624,440 A | 4/1997 | Huebner |
| 5,658,241 A | 8/1997 | Deharde et al. |
| 5,662,648 A | 9/1997 | Faccioli et al. |
| 5,662,650 A | 9/1997 | Bailey et al. |
| 5,672,175 A | 9/1997 | Martin |
| 5,681,313 A | 10/1997 | Diez |
| 5,685,830 A | 11/1997 | Bonutti |
| 5,695,496 A | 12/1997 | Orsak et al. |
| 5,728,172 A | 3/1998 | Krieger |
| 5,803,924 A | 9/1998 | Oni et al. |
| 5,823,931 A | 10/1998 | Gilmour |
| 5,873,843 A | 2/1999 | Draper |
| 5,976,125 A | 11/1999 | Graham et al. |
| 5,976,136 A | 11/1999 | Bailey et al. |
| 6,010,474 A | 1/2000 | Wycoki |
| 6,013,103 A | 1/2000 | Kaufman et al. |
| 6,036,691 A | 3/2000 | Richardson et al. |
| 6,162,223 A | 12/2000 | Orsak et al. |
| 6,176,860 B1 | 1/2001 | Howard |
| 6,264,696 B1 | 7/2001 | Reigner et al. |
| 6,277,124 B1 | 8/2001 | Haag |
| 6,471,664 B1 | 10/2002 | Campbell et al. |
| 6,494,914 B2 | 12/2002 | Brown et al. |
| 6,527,733 B1 | 3/2003 | Ceriani et al. |
| 6,540,708 B1 | 4/2003 | Manspeizer |
| 6,599,322 B1 | 7/2003 | Amrich et al. |
| 6,620,332 B2 | 9/2003 | Amrich |
| 6,752,775 B2 | 6/2004 | Seligman et al. |
| 6,764,457 B2 | 7/2004 | Hogg |
| 6,875,235 B2 | 4/2005 | Ferree |
| 6,972,020 B1 | 12/2005 | Grayson et al. |
| 7,018,418 B2 | 3/2006 | Amrich et al. |
| 7,029,475 B2 | 4/2006 | Panjabi |
| 7,150,721 B2 | 12/2006 | Houser |
| 7,188,626 B2 | 3/2007 | Foley et al. |
| 7,201,728 B2 | 4/2007 | Sterling |
| 7,235,102 B2 | 6/2007 | Ferree et al. |
| 7,241,298 B2 | 7/2007 | Nemec et al. |
| 7,247,157 B2 | 7/2007 | Prager et al. |
| 7,291,171 B2 | 11/2007 | Ferree |
| 7,393,335 B2 | 7/2008 | Carvey et al. |
| 2002/0052568 A1 | 5/2002 | Houser et al. |
| 2002/0068979 A1 | 6/2002 | Brown et al. |
| 2003/0109817 A1 | 6/2003 | Berl |
| 2003/0149386 A1 | 8/2003 | Ceriani et al. |
| 2004/0260302 A1 | 12/2004 | Manspeizer |
| 2004/0267179 A1 | 12/2004 | Lerman |
| 2005/0055025 A1 | 3/2005 | Zacouto et al. |
| 2005/0251080 A1 | 11/2005 | Hyde, Jr. |
| 2005/0261680 A1 | 11/2005 | Draper |
| 2006/0064169 A1 | 3/2006 | Ferree |
| 2006/0094989 A1 | 5/2006 | Scott et al. |
| 2006/0116616 A1 | 6/2006 | Albrecht et al. |
| 2006/0142680 A1 | 6/2006 | Iarocci |
| 2006/0241640 A1 | 10/2006 | Briard et al. |
| 2007/0053963 A1 | 3/2007 | Hotchkiss |
| 2008/0275555 A1 | 11/2008 | Makower et al. |
| 2008/0275558 A1 | 11/2008 | Clifford et al. |
| 2008/0275560 A1 | 11/2008 | Clifford et al. |
| 2008/0275562 A1 | 11/2008 | Clifford et al. |
| 2008/0275567 A1 | 11/2008 | Makower et al. |
| 2008/0275571 A1 | 11/2008 | Clifford et al. |
| 2010/0145449 A1* | 6/2010 | Makower .................. A61F 2/08 623/13.14 |
| 2012/0221121 A1* | 8/2012 | Draper ............... A61B 17/6425 623/46 |

OTHER PUBLICATIONS

Partial European Search Report for European Patent App. No. 10825425.1 (Feb. 12, 2015).

Office Action from U.S. Appl. No. 13/827,849 dated Apr. 7, 2014.

\* cited by examiner

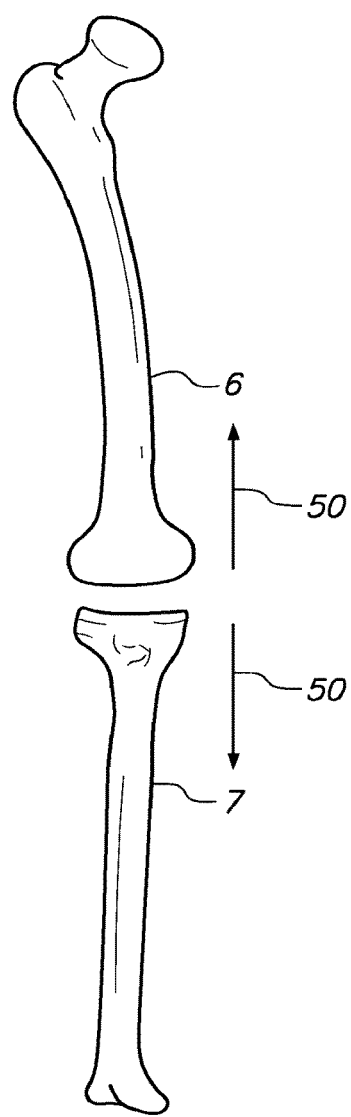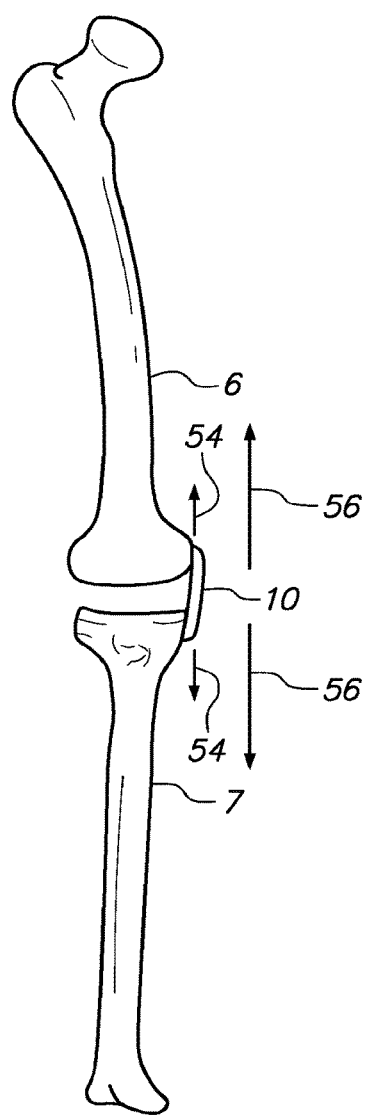

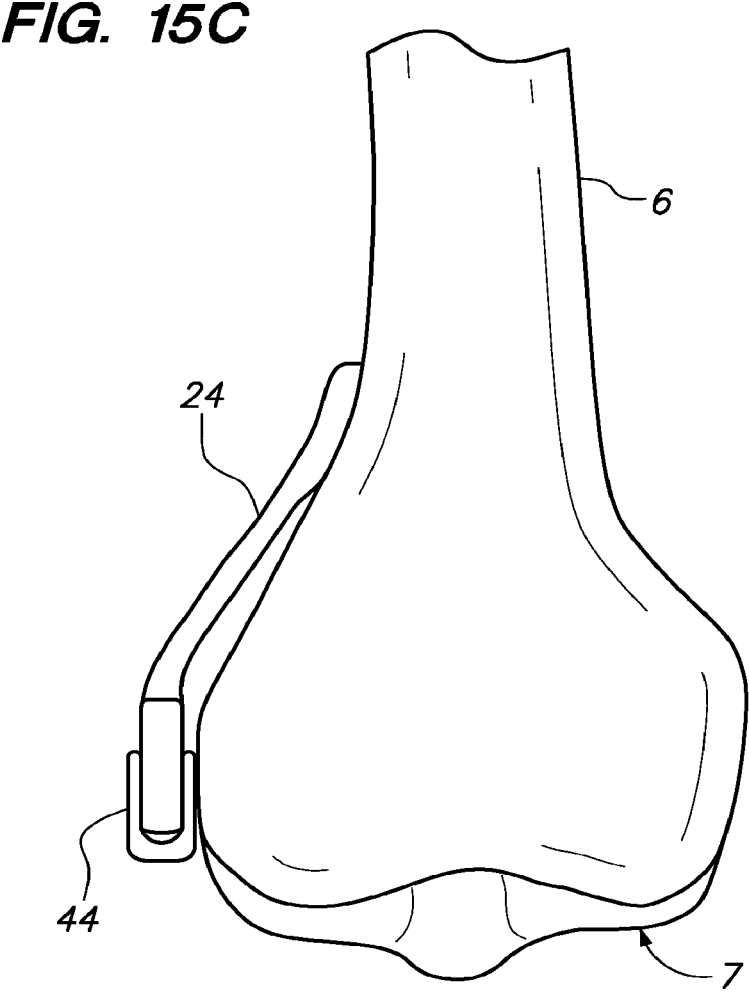

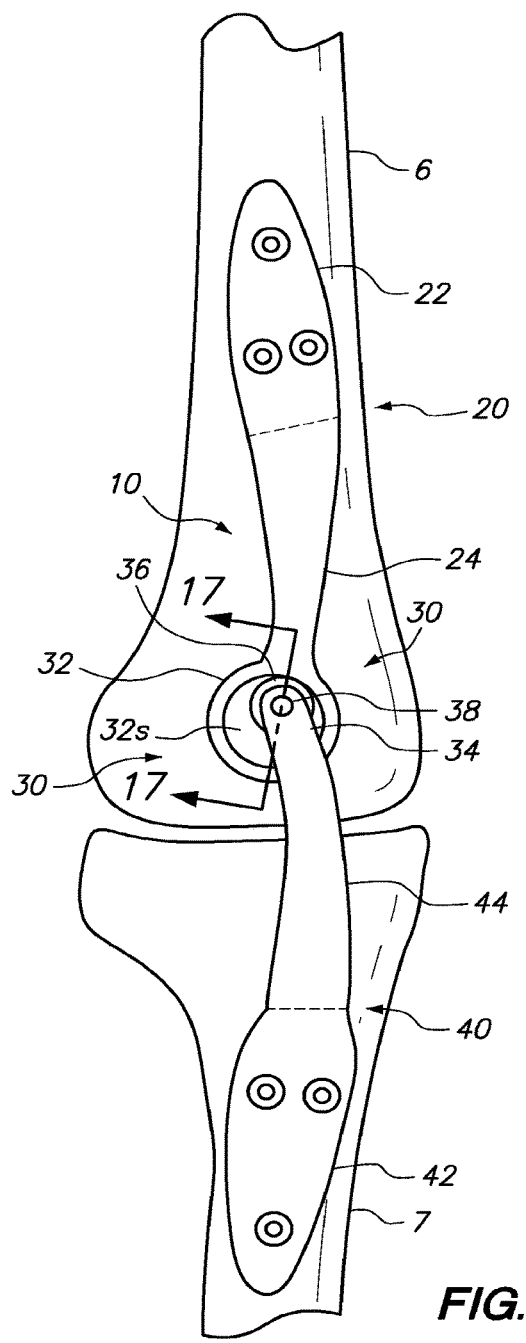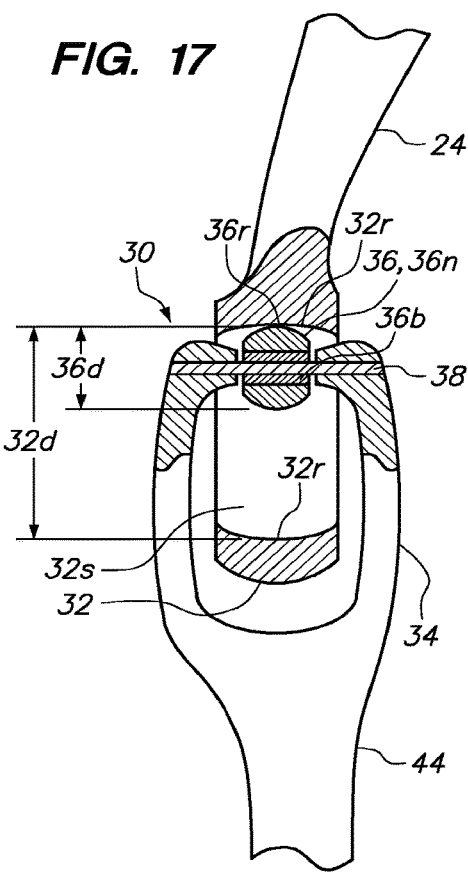
FIG. 17
FIG. 16

EXTRA-ARTICULAR IMPLANTABLE MECHANICAL ENERGY ABSORBING ASSEMBLIES HAVING TWO DEFLECTING MEMBERS AND METHODS

This application is a continuation of U.S. application Ser. No. 12/582,178, filed Oct. 20, 2009, the entire disclosures of which are expressly incorporated herein by reference.

FIELD OF THE INVENTION

The present invention is directed towards systems and methods for treating tissue of a body and more particularly, towards approaches designed to reduce mechanical energy transferred between members forming an anatomical joint.

BACKGROUND OF THE INVENTION

An anatomical joint is the location at which two or more bones make contact. They are constructed to allow movement and provide mechanical support, and are classified structurally and functionally. Structural classification is determined by how the bones connect to each other, while functional classification is determined by the degree of movement between the articulating bones. In practice, there is significant overlap between the two types of classifications.

There are three structural classifications of anatomical joints, namely fibrous or immovable anatomical joints, cartilaginous anatomical joints and synovial anatomical joints. Fibrous/Immovable bones are connected by dense connective tissue, consisting mainly of collagen. The fibrous joints are further divided into three types:

sutures which are found between bones of the skull;
syndesmosis which are found between long bones of the body; and
gomphosis which is an anatomical joint between the root of a tooth and the sockets in the maxilla or mandible.

Cartilaginous bones are connected entirely by cartilage (also known as "synchondroses"). Cartilaginous joints allow more movement between bones than a fibrous joint but less than the highly mobile synovial joint An example of a cartilaginous joint is an intervertebral disc. Synovial joints have a space between the articulating bones for synovial fluid. This classification contains anatomical joints that are the most mobile of the three, and includes the knee and shoulder. These are further classified into ball and socket joints, condyloid joints, saddle joints, hinge joints, pivot joints, and gliding joints.

Anatomical joints can also be classified functionally, by the degree of mobility they allow. Synarthrosis joints permit little or no mobility. They can be categorized by how the two bones are joined together. That is, synchrondoses are anatomical joints where the two bones are connected by a piece of cartilage. Synostoses are where two bones that are initially separated eventually fuse together as a child approaches adulthood. By contrast, amphiarthrosis joints permit slight mobility. The two bone surfaces at the anatomical joint are both covered in hyaline cartilage and joined by strands of fibrocartilage. Most amphiarthrosis joints are cartilaginous.

Finally, diarthrosis joints permit a variety of movements (e.g. flexion, adduction, pronation). Only synovial joints are diarthrodial and they can be divided into six classes: 1. ball and socket—such as the shoulder or the hip and femur; 2. Hinge—such as the elbow; 3. Pivot—such as the radius and ulna; 4. condyloidal (or ellipsoidal)—such as the wrist between radius and carps, or knee: 5. Saddle—such as the anatomical joint between carpal thumbs and metacarpals; and 6. Gliding—such as between the carpals.

Synovial joints (or diarthroses, or diarthroidal joints) are the most common and most moveable type of anatomical joints in the body. As with all other anatomical joints in the body, synovial joints achieve movement at the point of contact of the articulating bones. Structural and functional differences distinguish the synovial joints from the two other types of anatomical joints in the body, with the main structural difference being the existence of a cavity between the articulating bones and the occupation of a fluid in that cavity which aids movement. The whole of a diarthrosis is contained by a ligamentous sac, the joint capsule or articular capsule. The surfaces of the two bones at the anatomical joint are covered in cartilage. The thickness of the cartilage varies with each anatomical joint, and sometimes may be of uneven thickness. Articular cartilage is multi-layered. A thin superficial layer provides a smooth surface for the two bones to slide against each other. Of all the layers, it has the highest concentration of collagen and the lowest concentration of proteoglycans, making it very resistant to shear stresses. Deeper than that is an intermediate layer, which is mechanically designed to absorb shocks and distribute the load efficiently. The deepest layer is highly calcified, and anchors the articular cartilage to the bone. In anatomical joints where the two surfaces do not fit snugly together, a meniscus or multiple folds of fibro-cartilage within the anatomical joint correct the fit, ensuring stability and the optimal distribution of load forces. The synovium is a membrane that covers all the non-cartilaginous surfaces within the joint capsule. It secretes synovial fluid into the anatomical joint, which nourishes and lubricates the articular cartilage. The synovium is separated from the capsule by a layer of cellular tissue that contains blood vessels and nerves.

Cartilage is a type of dense connective tissue and as noted above, it forms a critical part of the functionality of a body (anatomical) joint. It is composed of collagenous fibers and/or elastin fibers, and cells called chondrocytes, all of which are embedded in a firm gel-like ground substance called the matrix. Articular cartilage is avascular (contains no blood vessels) and nutrients are diffused through the matrix. Cartilage serves several functions, including providing a framework upon which bone deposition can begin and supplying smooth surfaces for the movement of articulating bones. Cartilage is found in many places in the body including the anatomical joints, the rib cage, the ear, the nose, the bronchial tubes and between intervertebral discs. There are three main types of cartilage: hyaline, elastic and fibrocartilage.

Chondrocytes are the only cells found in cartilage. They produce and maintain the cartilaginous matrix. Experimental evidence indicates that cells are sensitive to their mechanical (stress-strain) state, and react directly to mechanical stimuli. The biosynthetic response of chondrocytes was found to be sensitive to the frequency and amplitude of loading (Wong et al., 1999 and Kurz et al., 2001). Recent experimental studies further indicate that excessive, repetitive loading may induce cell death, and cause morphological and cellular damage, as seen in degenerative joint disease (Lucchinetti et al., 2002 and Sauerland et al., 2003). Islam et al. (2002) found that continuous cyclic hydrostatic pressure (5 MPa, 1 Hz for 4 hours) induced apoptosis in human chondrocytes derived from osteoarthritic cartilage in vitro. In contrast, cyclic, physiological-like loading was found to trigger a partial recovery of morphological and ultra-structural aspects in osteoarthritic human articular chondrocytes (Nerucci et al., 1999).

Cancellous bone (also known as trabecular, or spongy) is a type of osseous tissue which also forms an important aspect of an anatomical joint. Cancellous bone has a low density and strength but very high surface area, that fills the inner cavity of long bones. The external layer of cancellous bone contains red bone marrow where the production of blood cellular components (known as hematopotesis) takes place. Cancellous bone is also where most of the arteries and veins of bone organs are found. The second type of osseous tissue is known as cortical bone, forming the hard outer layer of bone organs.

Various maladies can affect the anatomical joints, one of which is arthritis. Arthritis is a group of conditions where there is damage caused to the joints of the body. Arthritis is the leading cause of disability in people over the age of 65.

There are many forms of arthritis, each of which has a different cause. Rheumatoid arthritis and psoriatic arthritis are autoimmune diseases in which the body is attacking itself. Septic arthritis is caused by joint infection. Gouty arthritis is caused by deposition of uric acid crystals in the joint that results in subsequent inflammation. The most common form of arthritis, osteoarthritis is also known as degenerative joint disease and occurs following trauma to the anatomical joint, following an infection of the joint or simply as a result of aging.

Unfortunately, all arthritides feature pain. Patterns of pain differ among the arthritides and the location. Rheumatoid arthritis is generally worse in the morning; in the early stages, patients often do not have symptoms following their morning shower.

Osteoarthritis (OA, also known as degenerative arthritis or degenerative joint disease, and sometimes referred to as "arthrosis" or "osteoarthrosis" or in more colloquial terms "wear and tear"), is a condition in which low-grade inflammation results in pain in the joints, caused by wearing of the cartilage that covers and acts as a cushion inside joints. As the bone surfaces become less well protected by cartilage, the patient experiences pain upon weight bearing, including walking and standing. Due to decreased movement because of the pain, regional muscles may atrophy, and ligaments may become more lax. OA is the most common form of arthritis.

The main symptoms of osteoarthritis is chronic pain, causing loss of mobility and often stiffness. "Pain" is generally described as a sharp ache, or a burning sensation in the associated muscles and tendons. OA can cause a crackling noise (called "crepitus") when the affected anatomical joint is moved or touched, and patients may experience muscle spasm and contractions in the tendons. Occasionally, the joints may also be filled with fluid. Humid weather increases the pain in many patients.

OA commonly affects the hand, feet, spine, and the large weight-bearing anatomical joints, such as the hips and knees, although in theory, any anatomical joint in the body can be affected. As OA progresses, the affected joints appear larger, are stiff and painful, and usually feel worse, the more they are used and loaded throughout, the day, thus distinguishing it from rheumatoid arthritis. With progression in OA, cartilage looses its viscoelastic properties and its ability to absorb load.

Generally speaking, the process of clinical detectable osteoarthritis is irreversible, and typical treatment consists of medication or other interventions that can reduce the pain of OA and thereby improve the function of the anatomical joint. According to an article entitled "Surgical approaches for osteoarthritis" by Klaus-Peter Günther, MD, over recent decades, a variety of surgical procedures have been developed with the aim of decreasing or eliminating pain and improving function in patients with advanced osteoarthritis (OA). The different approaches include preservation or restoration of articular surfaces, total joint replacement with artificial implants, and arthrodeses.

Arthrodeses are described as being reasonable alternatives for treating OA of small hand and foot joints as well as degenerative disorders of the spine, but were deemed to be rarely indicated in large weight-bearing anatomical joints such as the knee doe to functional impairment of gait, cosmetic problems and further side-effects. Total joint replacement was characterized as an extremely effective treatment for severe joint disease. Moreover, recently developed joint-preserving treatment modalities were identified as having a potential to stimulate the formation of a new articular surface in the future. However, it was concluded that such techniques do not presently predictably restore a durable articular surface to an osteoarthritic joint. Thus, the correction of mechanical abnormalities by osteotomy and joint debridement are still considered as treatment options in many patients. Moreover, patients with limb malalignment, instability and intra-articular causes of mechanical dysfunction can benefit from an osteotomy to provide pain relief, with the goal being the transfer of weight-bearing forces from arthritic portions to healthier locations of an anatomical joint.

Joint replacement is one of the most common and successful operations in modern orthopedic surgery. It consists of replacing painful arthritic, worn, or diseased parts of the anatomical joint with artificial surfaces shaped in such a way as to allow joint movement. Such procedures are a last resort treatment as they are highly invasive and require substantial periods of recovery. Some forms of joint replacement are referred to as total joint replacement indicating that all anatomical joint surfaces are replaced. This contrasts with hemiarthroplasty (half arthroplasty) in which only one bone's anatomical joint surface is replaced and unicompartmental arthroplasty in which both surfaces of the knee, for example, are replaced but only on the inner or outer sides, not both. Thus, arthroplasty, as a general term, is an operative procedure of orthopedic surgery performed, in which the arthritic or dysfunctional joint surface is replaced with something better or by remodeling or realigning the anatomical joint by osteotomy or some other procedure. These procedures are also characterized by relatively long recovery times and are highly invasive procedures. The currently available therapies are not condro-protective. Previously, a popular form of arthroplasty was interpositional arthroplasty with interposition of some other tissue like skin, muscle or tendon to keep inflammatory surfaces apart or excisional arthroplasty in which the joint surface and bone was removed leaving scar tissue to fill in the gap. Other forms of arthroplasty include resection(al) arthroplasty, resurfacing arthroplasty, mold arthroplasty, cup arthroplasty, silicone replacement arthroplasty, etc. Osteotomy to restore or modify joint congruity is also an arthroplasty.

Osteotomy is a related surgical procedure involving cutting of bone to improve alignment. The goal of osteotomy is to relieve pain by equalizing forces across the joint as well as increase the lifespan of the joint. This procedure is often used in younger, more active or heavier patients. High tibial osteotomy (HTO) is associated with a decrease in pain and improved function. However, HTO does not address ligamentous instability—only mechanical alignment. HTO is associated with good early results, but results typically deteriorate over time.

Other approaches to treating osteoarthritis involve an analysis of loads that exist at a joint. Both cartilage and bone are living tissues that respond and adapt to the loads they experience. If an anatomical joint surface remains unloaded for appreciable periods of time the cartilage tends to soften and weaken. Further, as with most materials that experience structural loads, particularly cyclic structural loads, both bone and cartilage begin to show signs of failure at loads that are below their ultimate strength. However, cartilage and bone have some ability to repair themselves. There is also a level of load at which the skeleton will fail catastrophically. Accordingly, it has been concluded that the treatment of osteoarthritis and other conditions is severely hampered when a surgeon is not able to precisely control and prescribe the levels of anatomical joint load. Furthermore, bone healing research has shown that some mechanical stimulation can enhance the healing response and it is likely that the optimum regime for a cartilage/bone graft or construct will involve different levels of load over time, e.g. during a particular treatment schedule. Thus, there has been identified a need for devices which facilitate the control of load on an anatomical joint undergoing treatment or therapy, to thereby enable use of the anatomical joint within a healthy loading zone.

Certain other approaches to treating osteoarthritis contemplate external devices such as braces or fixators which control the motion of the bones at an anatomical joint or apply cross-loads at an anatomical joint to shift load from one side of the anatomical joint to the other. Various of these approaches have had some success in alleviating pain but suffer from patient compliance or lack an ability to facilitate and support the natural motion and function of the diseased anatomical joint. Notably, the motion of bones forming an anatomical joint can be as distinctive as a finger print, and thus, each individual has his or her own unique set of problems to address. Therefore, mechanical approaches to treating osteoarthritis have had limited applications.

Prior approaches to treating osteoarthritis have also been remiss in acknowledging all of the basic functions of the various structures of an anatomical joint in combination with its unique movement. That is, in addition to addressing loads at an anatomical joint and anatomical joint movement, there has not been an approach which also acknowledges the dampening and energy absorption functions of the anatomy, and taking a minimally invasive approach in implementing solutions. Prior devices designed to reduce the load transferred by the anatomical joint typically describe rigid body systems that are incompressible. Mechanical energy is the product of force (F) and displacement distance (s) of a given mass (i.e., E=F×s, for a given mass M). These systems have zero displacement within their working body (s=0). Since there is no displacement within the device it is reasonable to say that, there is no energy-storage or absorption in the device. Such devices act to transfer and not absorb energy from the anatomical joint. By contrast the anatomical joint is not a rigid body but is comprised of elements of different compliance characteristics such as bone, cartilage, synovial fluid, muscles, tendons, ligaments, etc. as described above. These dynamic elements act to both transfer and absorb energy about the anatomical joint. For example cartilage compresses under applied force and therefore the resultant force displacement product represents the energy absorbed by cartilage. In addition cartilage has a non linear force displacement-behavior and is considered viscoelastic. Such systems not only absorb and store, but additionally act to dissipate energy.

Therefore, approaches to treating anatomical joint pain are needed that address both anatomical joint movement and varying loads as well as dampening forces and energy absorption provided by an articulating joint.

The present invention satisfies these and other needs.

SUMMARY OF THE INVENTION

The present invention provides implantable assemblies for manipulating energy transferred by members defining an anatomical joint, and methods of implanting and using the same.

An implantable assembly is provided, including a first component configured to be attached to a first anatomical member of an articulating anatomical joint; a second component configured to be attached to a second member of the anatomical joint; and a joint joining said first and second components; wherein the first component includes a first flex member, the first flex member configured to deflect, bend or twist to absorb energy transferred from the first component to the second component when the distance between the first and second components becomes smaller than an implant-defined distance.

In at least one embodiment, the second component includes a second flex member.

In at least one embodiment, the first and second flex members are configured to flex in a direction substantially normal to a direction of bending of the anatomical joint.

In at least one embodiment, the first component further comprises a first base configured to be attached to the first member, and the first flex member is fixed to or integral with the first base; and wherein the second component further comprises a second base configured to be attached to the second member, and the second flex member is fixed to or integral with the second base.

In at least one embodiment, the joint comprises a compliance member mounted between end portions of the first and second components.

In at least one embodiment, the first component comprises a ring shaped end and the second component comprise a shackle.

In at least one embodiment, the joint comprises a compliance member within the ring shaped end and connected to the shackle.

In at least one embodiment the compliance member comprises an outside diameter that is much less than an inside diameter of the ring-shaped end, thereby leaving space within a ring formed by the ring-shaped end.

In at least one embodiment, the compliance member fills an entire space of a ring formed by the ring-shaped end.

In at least one embodiment, the joint permits relative axial rotations between the first and second components.

In at least one embodiment, the anatomical joint is a knee joint, the first component is adapted to be fixed to a femur of the knee joint and second component is adapted to be fixed to a tibia of the knee joint.

In at least one embodiment, the first and second flex members Ilex and absorb energy from the forces applied by the members of the anatomical joint, thereby relieving at least a portion of the load resultant from the forces from being transferred through contacting surfaces of the anatomical joint.

In at least one embodiment, the assembly relieves load on a side of the anatomical joint to which the assembly is attached.

In at least one embodiment, the assembly includes a pin, and the compliance member is attached to the shackle via the pin.

In at least one embodiment, the compliance member is free to rotate relative to the shackle, about the pin.

A method for treating an anatomical joint is provided that includes attaching a first component of an assembly to a first anatomical member of the anatomical joint; and attaching a second component of the assembly to a second anatomical member of the anatomical joint; wherein a joint of the assembly joins the first and second components, the first component includes a first flex member and the second component includes a second flex member; and flexing the first and second flex members to transiently variably reduce load between the first and second anatomical members of the anatomical joint, wherein the assembly is implanted.

In at least one embodiment, the method further includes permitting at least a limited amount of axial rotation between the first and second anatomical members of the anatomical joint.

In at least one embodiment, the first and second components are attached at locations to place the joint adjacent to a location of the anatomical joint that translates very little over a range of motion of the anatomical joint, relative to other locations on foe anatomical joint.

In at least one embodiment, the anatomical joint is a knee joint, and the location that translates very little is about the midpoint of a Blumensaat's line of a femur of the knee joint.

In at least one embodiment, the method includes temporarily fixing the joint at the location of the anatomical joint that translates very little prior to the attaching a first component and attaching a second component, and treeing the joint from the temporarily fixing prior to completion of implantation of the assembly.

These and other features of the invention will become apparent to those persons skilled in the art upon reading the details of the assemblies and methods as more fully described below.

BRIEF DESCRIPTION OF THE DRAWINGS

FIG. 1 is a front view, illustrated normal forces existing in a joint.

FIG. 2 is a front view, depicting the effect an energy manipulating assembly of the present invention has on the joint shown in FIG. 1.

FIG. 15A-15C illustrate the assembly of FIG. 12 at various phases of flexion/extension of the knee joint. FIG. 15A also illustrates an optional sheath provided over at least a portion of the assembly of FIG. 12.

FIG. 16 is a side view of another embodiment of an assembly according to the present invention, installed on a knee joint.

FIG. 17 is an enlarged partial sectional view of the joint portion of the assembly of FIG. 16.

DETAILED DESCRIPTION OF THE INVENTION

Figure 3:
FIG. 3 is a graph of force versus displacement, illustrating the energy characteristics of a prior art rigid structure applied across a joint.

Before the present devices and methods are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. Thus, for example, reference to "a screw" includes a plurality of such screws and reference to "the device" includes reference to one or more devices and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Referring now to the drawings, which are provided by way of example and not limitation, the present invention is directed towards devices and methods for treating body tissues. In applications relating to the treatment of body (anatomical) joints, the present invention seeks to alleviate pain associated with the function of diseased, overloaded or malaligned members forming an anatomical joint. Whereas the present invention is particularly suited to address issues associated with osteoarthritis, the energy manipulation accomplished by the present invention lends itself well to broader applications. Moreover, the present invention is particularly suited to treating synovial joints such as the knee and shoulder, as well as other synovial or articular, cartilaginous joints of the body, such as those of the hips, fingers, wrist, ankles and toes. However, it is also contemplated that the apparatus and methods of the present invention can be employed to treat other non-synovial, non-articular, non-cartilaginous joints that are capable of motion in a flexion/extension direction that exceeds forty-five degrees.

In one particular aspect, the extra articular energy absorbing assemblies of the present invention seek to permit and complement the unique articulating motion of the members defining an anatomical joint of a patient while simultaneously manipulating energy being experienced by both cartilage and osseous tissue (cancellous and cortical bone). To minimize pain, transient variable load reduction or absorption of 1-40% of forces, in varying degrees, may be necessary. Transient variable load reduction or absorption in the range of 5-30% can be a target for certain applications. Transient variable load reduction or absorption refers to the function of the energy manipulation structure of the present invention reducing the load experienced by the joint during the joint's higher loading positions and the energy manipulation structure not reducing the load experienced by the joints during lower or no load positions. In certain specific applications, transient distraction is employed in the energy manipulation approach.

In order to implant the extra articular energy absorbing assemblies of the present invention, conventional surgical or minimally invasive approaches are used to gain access to an anatomical joint or other anatomy requiring attention. Arthroscopic approaches are contemplated when reasonable to both implant the energy manipulation assembly as well as to accomplish adjusting an implanted assembly. Biologically inert materials of various kinds are employed in constructing the energy manipulation assemblies of the present invention.

In one particular approach, an energy absorbing or manipulating device is provided in which multiple components deflect, bend side-to-side, or twist to manipulate or absorb forces/load between body parts that are joined at an anatomical joint, to which body parts the device is mounted. Thus, a device utilizing elements that can absorb forces/load applied by the bones that are joined by the joint may be desirable to treat afflictions such as osteoarthritis, trauma, or other pain-causing conditions in a joint. Preferably the embodiments of the present invention are implanted subcutaneously and are extra-articular, peri-articular or extra- or para-capsular of the treated anatomical joint.

The deflecting, bending or twisting of the energy absorbing assembly is used in a novel way in the present invention to accommodate the complex flexing, rotating and sliding motions of articulating anatomical joints such as the knee while utilizing fewer rotating or rubbing parts so as to decrease the generation of wear debris over the useful life of the assembly.

Referring to FIGS. 1-2, forces occurring between members forming an anatomical joint are described. The arrows 50 shown in FIG. 1 represent forces occurring between adjacent members 6, 7 of an anatomical joint lacking an energy manipulation assembly 10 of the present invention. However, as shown in FIG. 2, in body anatomy incorporating the present invention, less forces/load are transferred to the bones and cartilage of the members defining the anatomical joint. Where the anatomical joint is treated with the foregoing described energy manipulating assemblies of the present invention, a portion of the forces/load between body members is absorbed by the energy manipulating assembly 10 (depicted as arrows 54 in FIG. 2). Accordingly, with the energy manipulation assembly 10 in place, less force is placed on the joint than when the assembly 10 is not present. The total load in FIG. 2 is shared between the force/load 56 carried by the joint and the force/load 54 carried by the assembly 10.

The assembly 10 absorbs energy in the joint by application of a force in the direction of the arrows 54, which are generally in an axial direction of the joint in extension. The assembly 10 uses flex members to apply force in directions substantially opposite to the directions of load applied by the first and second members of the anatomical joint toward one another. This can also be described as applying a force in a direction of distraction, although actual distraction of the joint may or may not be present.

Although the assembly 10 is schematically represented as being installed on the medial side of the joint shown in FIG. 2, the present invention is not limited to such an arrangement, as assembly 10 can alternatively be installed on the lateral side of the joint, or a pair of assemblies 10 can alternatively be installed, one on the medial side of the joint and one on the lateral side of the joint.

Figure 4:
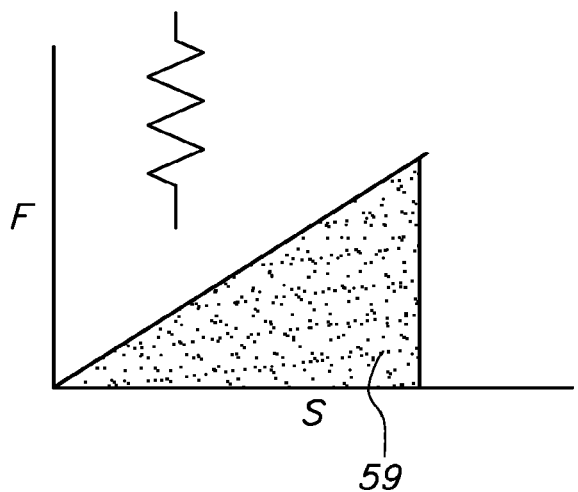
FIG. 4 is a graph, of force versus displacement, illustrating the energy characteristics of a linear spring system.
Figure 5:
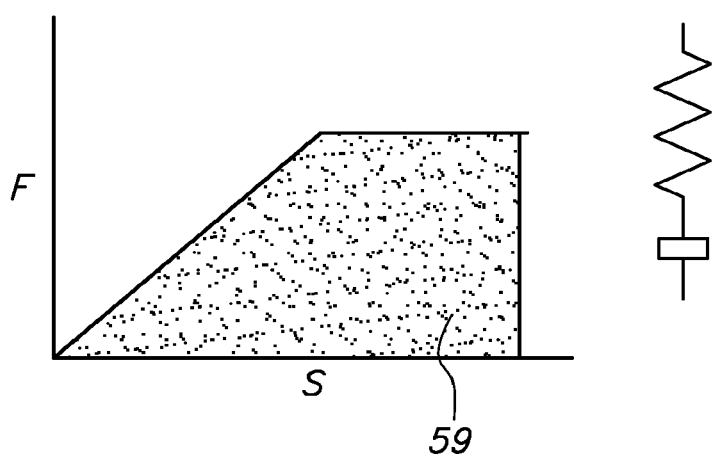
FIG. 5 is a graph of force versus displacement, illustrating the energy characteristics of a spring and dampening system.
Figure 6:
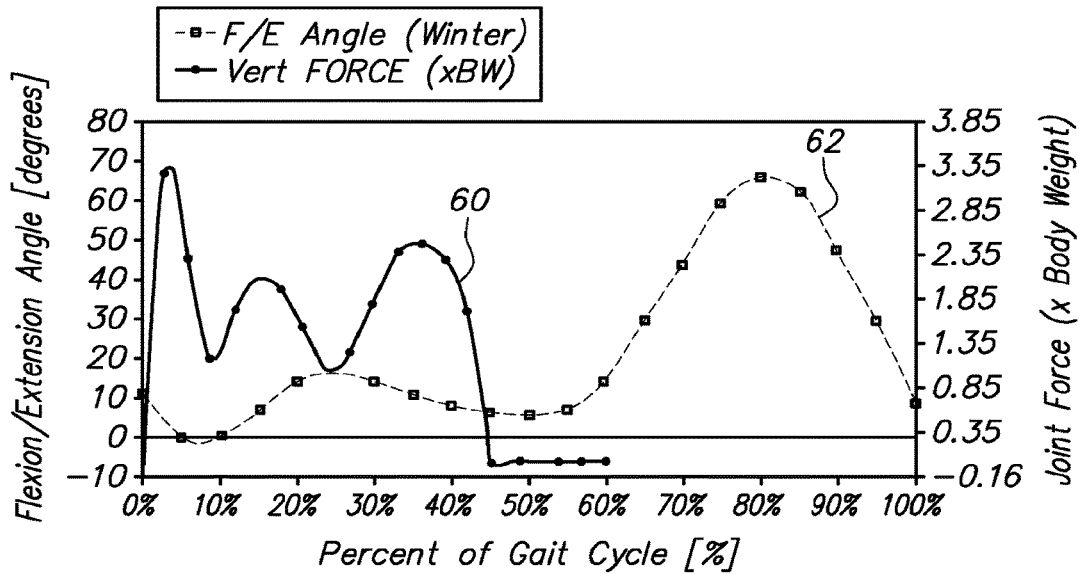
FIG. 6 is a graph, illustrating the flexion/extension angle and joint force existing in a gait cycle.

FIGS. 3-5 illustrate the relation between force (F) and displacement (S) between members of an anatomical joint (where mass is constant). In a rigid body system (FIG. 3) which does not incorporate aspects of the present invention, there is no displacement and no energy absorption. In an energy manipulating system incorporating a single linear spring (FIG. 4), energy is absorbed in proportion to a spring constant (spring stillness). The energy absorbed is represented by the shaded area 59 below the curve. As shown in FIG. 5, where a spring and dampener are used in combination, the energy absorbed 59 is a function of the spring constant and the dampener. It is these relationships which are considered in developing desired energy manipulating characteristics for an energy absorbing assembly for a joint.

Figure 7:
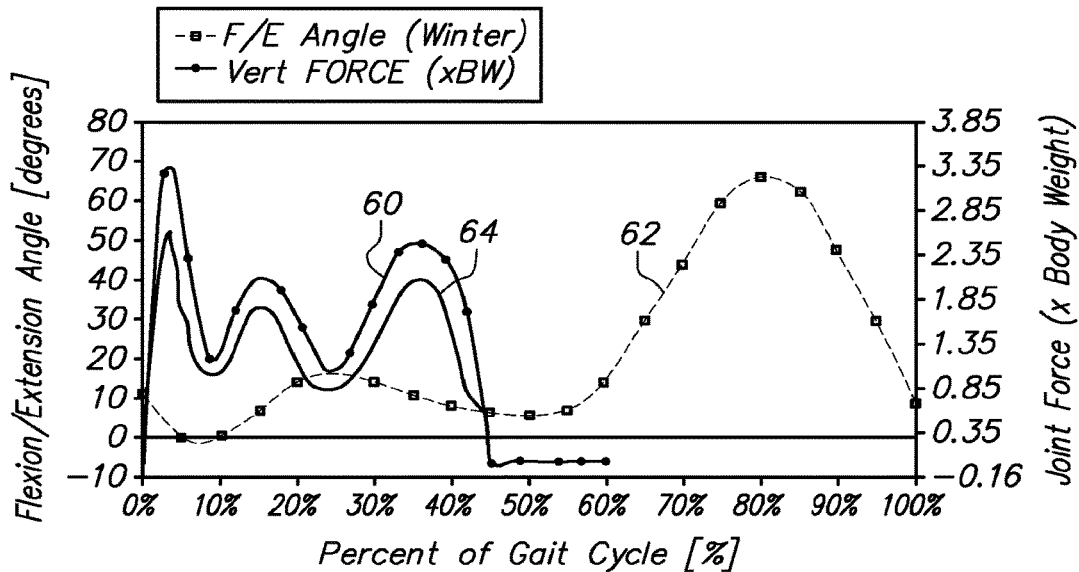
FIG. 7 is a graph, illustrating one approach to energy absorption on a gait cycle.
Figure 8:
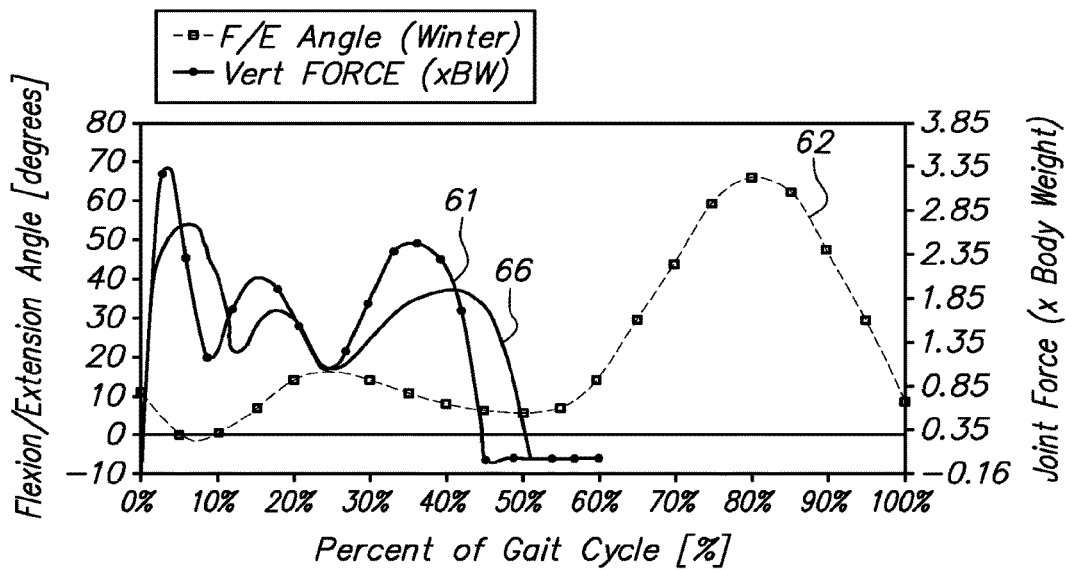
FIG. 8 is a graph, illustrating a second approach to energy absorption on a gait cycle.
Figure 9:
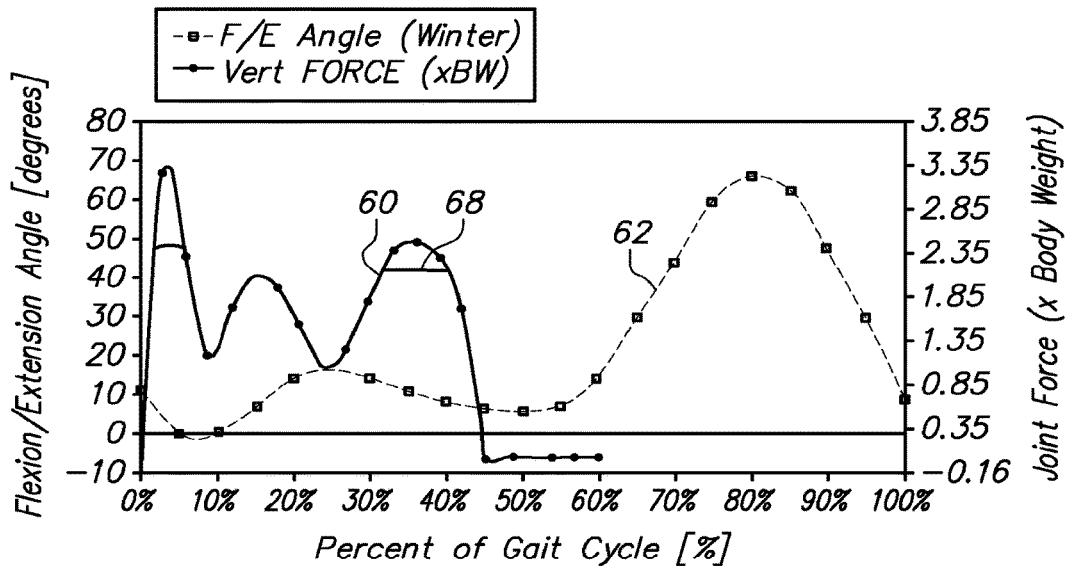
FIG. 9 is a graph, illustrating a third approach to energy absorption on a gait cycle.
Figure 10:
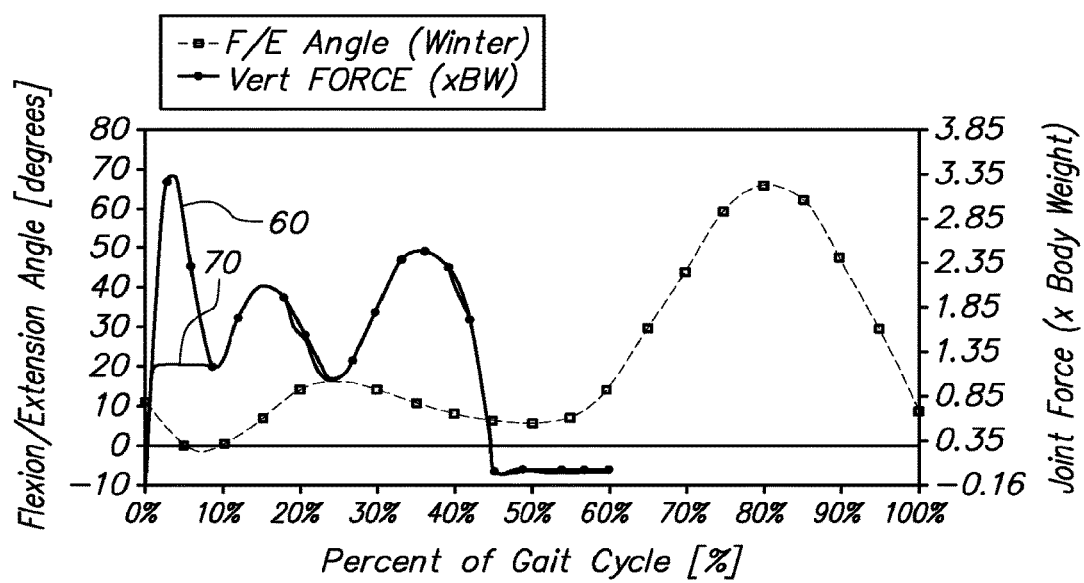
FIG. 10 is a graph, illustrating a fourth approach to energy absorption on a gait cycle.

Also considered are the forces existing through the flexion and extension through an articulation cycle of the particular joint anatomy to be treated. Using the gait cycle of the legs of a human as an example, both the joint force and flexion/extension angle in degrees for a knee joint during walking can be plotted versus the percentage of the gait cycle completed with the gait cycle beginning at heel contact. A normal or expected relationship 60 of vertical forces generated through the gait cycle is depicted in each of FIGS. 6-10. Also depicted in FIGS. 6-10 is the flexion/extension angle 62 of the knee throughout the gait cycle. The expected relationship 60 of vertical forces during the gait cycle can be altered using certain of the embodiments of the energy manipulation assemblies of the present invention. As shown in FIG. 7, an energy manipulation assembly 10 according to the present invention can absorb energy by a substantially fixed proportion during a portion of the gait cycle. This is reflected by curve 64 in FIG. 7. Moreover, energy can be both absorbed and dampened as represented by curve 66 of FIG. 8 or alternatively, energy can be absorbed only above a fixed value as represented by curve 68 of FIG. 9. Additionally, as reflected by curve 70 of FIG. 10, energy can be absorbed in a fixed portion of the gate cycle or though a limited range of motion of the joint. It is to be recognized, however, that each of or one or more of these types of energy absorption can be combined in a desired system.

Figure 11:
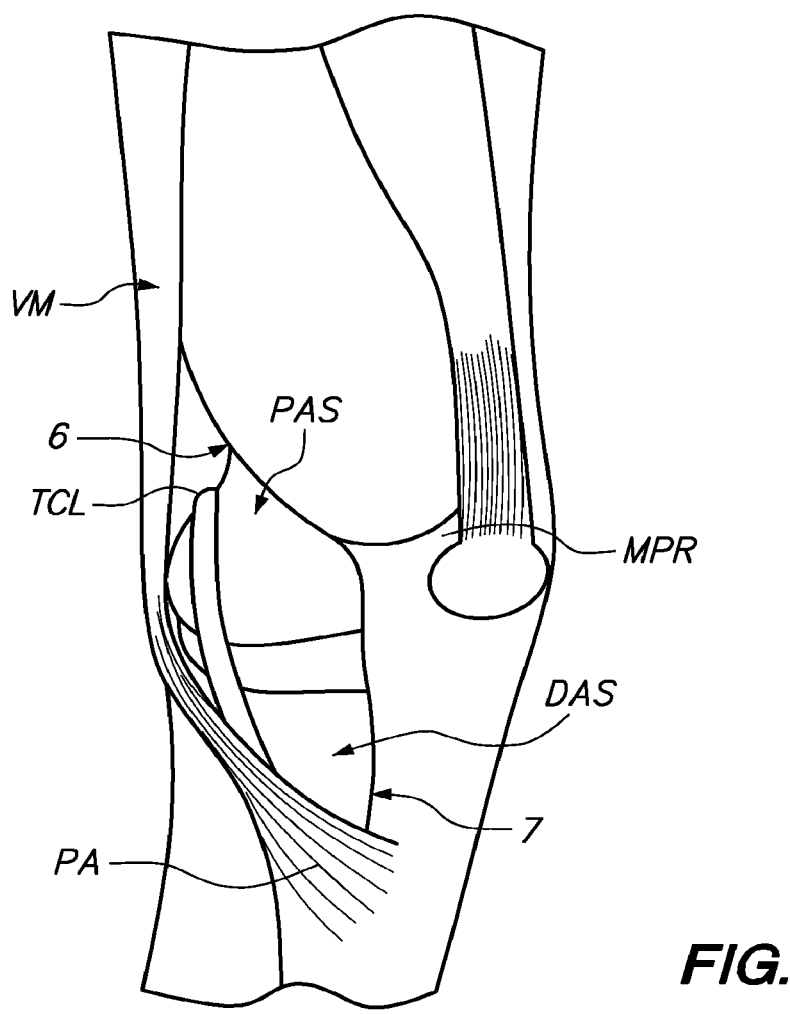
FIG. 11 is a perspective view, depicting anatomy of a typical knee joint.

Referring now to FIG. 11, the medial side anatomy of a typical knee joint is presented in a manner relating to an implantation procedure. Such a procedure could ultimately involve the implantation of devices such as those described below. Although the knee joint is being described here, it is contemplated that these devices can also be placed at other articular, cartilaginous joints throughout the body, and some non-articular, non-cartilaginous joints that are capable of motion in a flexion/extension direction that exceeds forty-five degrees.

In a procedure seeking to transiently, variably reduce load or manipulate forces at a knee joint, a proximal attachment site (PAS) for a base of an energy manipulation device must be identified. Similarly, a distal attachment site (DAS) must also be selected. In a contemplated approach the medial proximal attachment site (PAS) can be located on a femur 6 in a space defined by the medial patellar retinaculum (MPR), the vastus medialis (VM) and the tibial collateral ligament (TCL). The distal attachment site (DAS) can be located on the tibia in the region defined by the medial patellar retinaculum (MPR) and the pes anserinus (PA).

Figure 12:
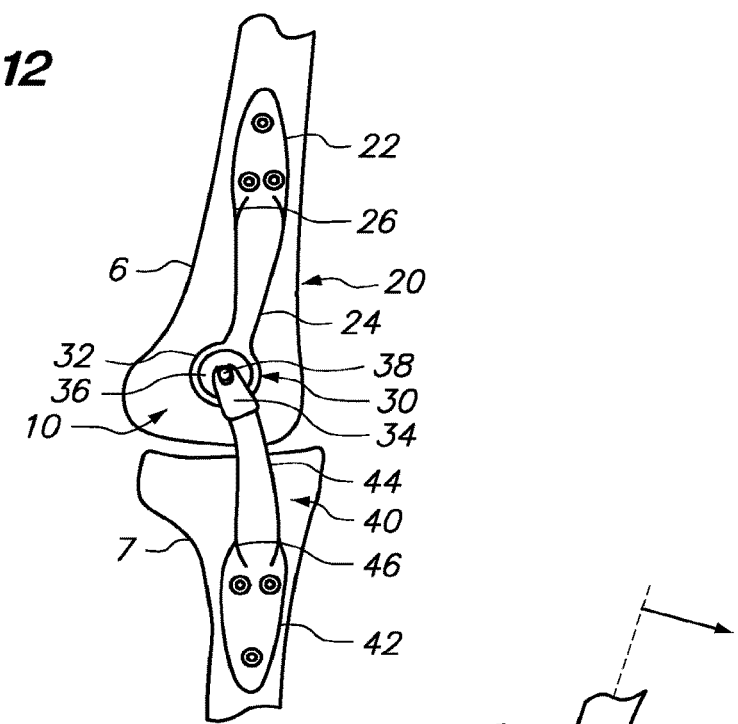
FIG. 12 is a side view of one embodiment of an assembly installed on a knee joint according to the present invention.
Figure 13:
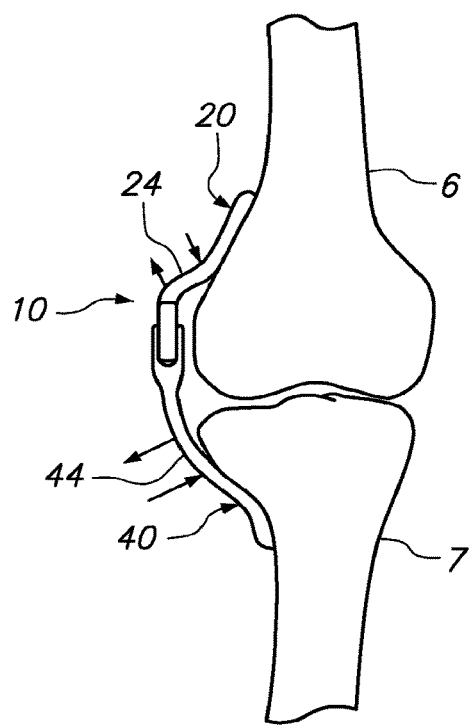
FIG. 13 is an anterior view of FIG. 12.

FIGS. 12-13 show a medial side view and an anterior view of one embodiment of an energy absorbing assembly 10 according to the present invention installed medially on a knee joint. Assembly 10 includes a first component 20 (in this example, first component 20 is a femoral component) and a second component 40 (in this example, second component 40 is a tibial component). The femoral component 20 is configured to be attached to a distal end portion of a patient's femur 6. The femoral component 20 includes a first base 22 that is configured to be anchored to a first bone that connects at the joint, and second component 40 includes a second base 42 that is configured to be anchored to a second bone that connects at the joint.

First component 20 includes a first flex member 24 that may be integral with first base 22, but is preferably removably fixed thereto at 26, such as by a dovetail connection with or without locking screw, or other mechanical connection that can be locked during use, but unlocked at any such time as separation of the base 22 and flex member 24 is desired. Likewise, second component 40 includes a second flex member 44 that may be integral with second base member 42, but is preferably removably fixed thereto at 46.

The opposite ends of flex members 24 and 44 that are not fixed to base members 22 and 42 are configured, to form rotational joint 30 such that the first and second components 20, 40 are joined at joint 30. In the example shown in FIG. 12, first component 20 ends as a ring member 32 that is integral with the end of flex member 24 that is opposite the end of flex member 24 fixed to base member 22, second component 40 ends as a shackle 34 that is pinned through ring member 32, as shown, it is noted here that joint 30 need not be configured to the specific arrangement shown in FIG. 12, as alternative arrangements could be provided. For example, first component 20 could be provided with shackle 34 and second component 40 could be provided with ring member 32. Further alternatively, any other structures could be provided that would form a connection between the two members 20 and 40 and perform as described below. This connection, however, does not require constant contact between the members forming the connection, as described in more detail below.

A compliance member 36 is provided between ring and shackle members 32 and 34. More specifically, in the embodiment shown, compliance member may be press fit, glued, or loosely fit within ring member 32 and pin 38 extends through an opening in compliance member 36 to fix compliance member to shackle 34. Compliance member 36 can be connected to ring member 32 using any type of connection that provides reliable "stack-up" height when needed to provide support to the joint. For example, in the ease of the knee joint, as the knee joint is extended or loaded, the connection between compliance member 36 and ring member 32 is able to transmit force therethrough. Outside of the anatomical joint angles where the apparatus does not need to provided unloading to the anatomical joint, compliance member 36 can be loose, e.g., not even in contact with ring member 32, and this may facilitate maintenance of full range of motion of the anatomical joint. Pin 38 is rigid and may be made of the same material as components 20 and 40 (e.g., titanium, stainless steel or other biocompatible metal or alloy). Note that "fix" is used here to describe the fact the compliance member 36 cannot escape from its connection to shackle 34, as pin 38 prevents this. However, pin 38 can allow rotation of compliance member 36 relative to shackle 34. Compliance member 36 may be provided with a sleeve or bushing 37 surrounding the opening through which pin 38 is inserted, to prevent erosion of the elastomeric material of compliance member 36 as it rotates relative to pin 38. Bushing 37 may be formed of any of the metals or alloys that can be used to make members 20, 40, or other hardened, biocompatible material.

Compliance member 36 may be formed as a flexible cylindrical member of an elastomeric material for example and, in the example shown, is an elastomeric disc. Examples of elastomeric materials include polymers such as polyethylene, polyurethane, and polycarbonates, silicone, polyester, and thermoplastics.

Figure 14:
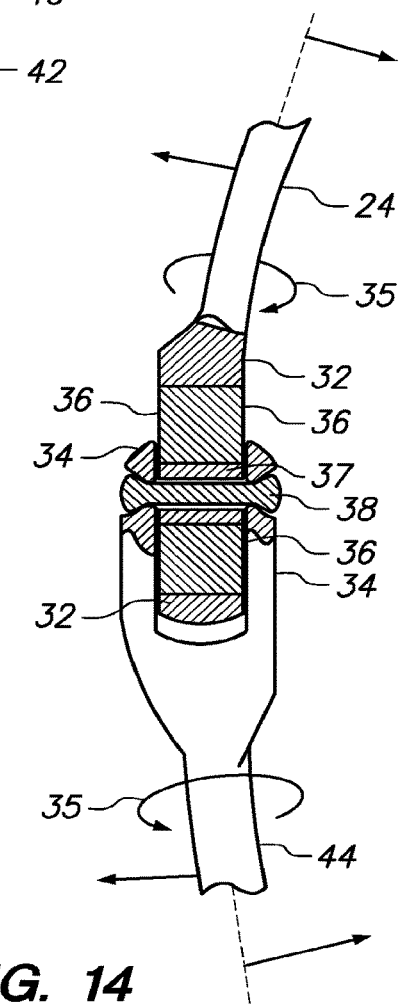
FIG. 14 is an enlarged partial sectional view of the joint portion of the assembly of FIGS. 12-13.

During loading of the anatomical joint (such as the knee during walking), the forces applied through assembly 10 cause flex members 24 and 44 to bend (flex) in directions indicated by the arrows A in FIG. 13. This results in joint 30 flexing out away from the natural joint somewhat with the flexing members 24, 44 taking up (absorbing) the distance change between components under loading of the natural joint. This flexing absorbs some of the energy of the forces, thereby reducing the amount of force/load that is applied through, the natural joint, as was described above. The flexing of the members 24, 44 also alters the angle at which the ring and shackle members 32 and 34 are oriented. The compliance member 36 deforms (e.g. compresses on one side and extends on the opposite side of the ring) to compensate for this change of angle. Additionally, compliance member 38 can deform (e.g., twist) to accommodate relative axial rotation between components 20, 40 (e.g., see arrows 35 in FIG. 14). During flexion of the natural joint, the forces are also removed from flex members 24, 44 and they relax from the bent or twisted configurations.

Figure 15A:
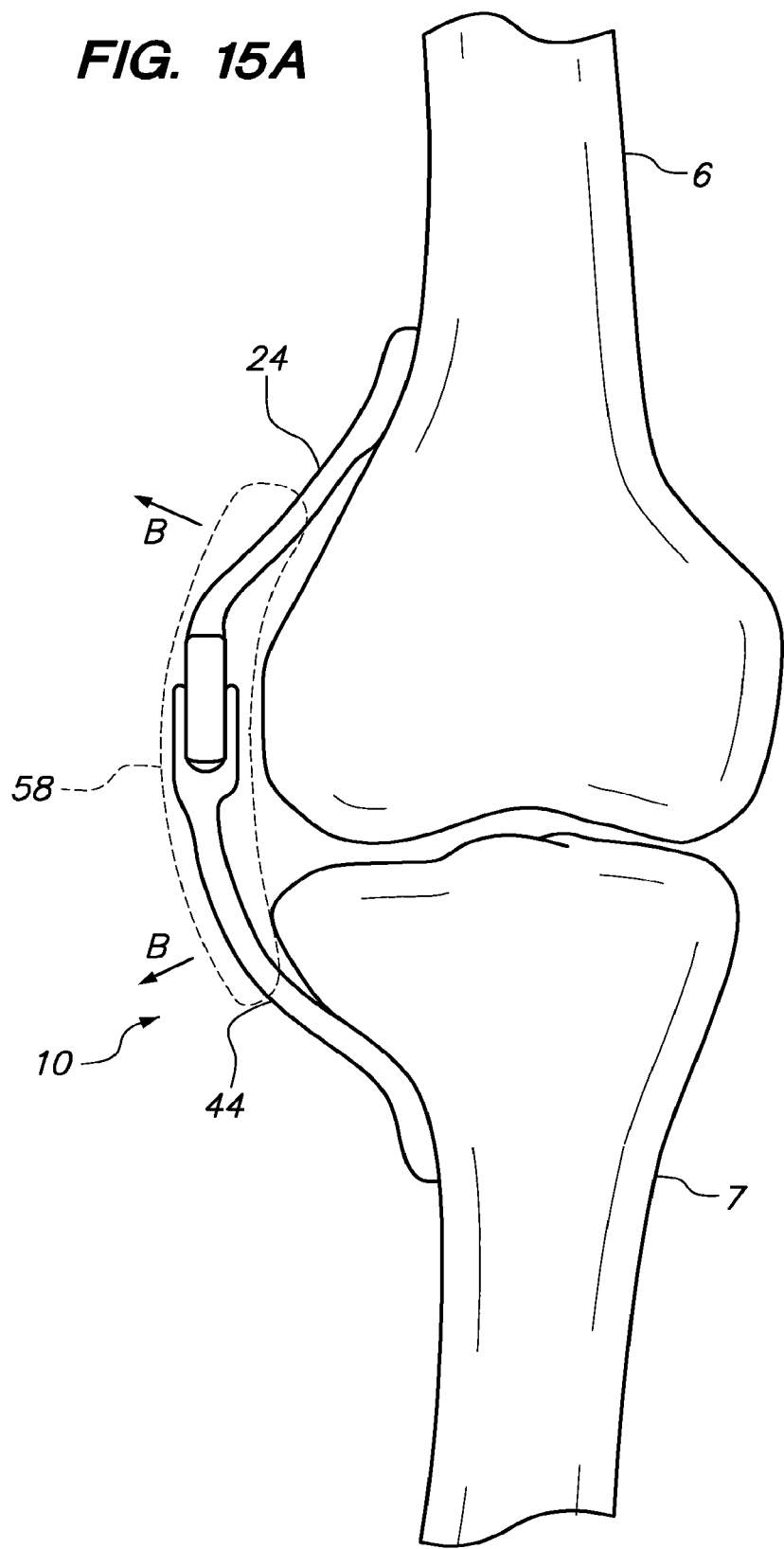
Figure 15B:
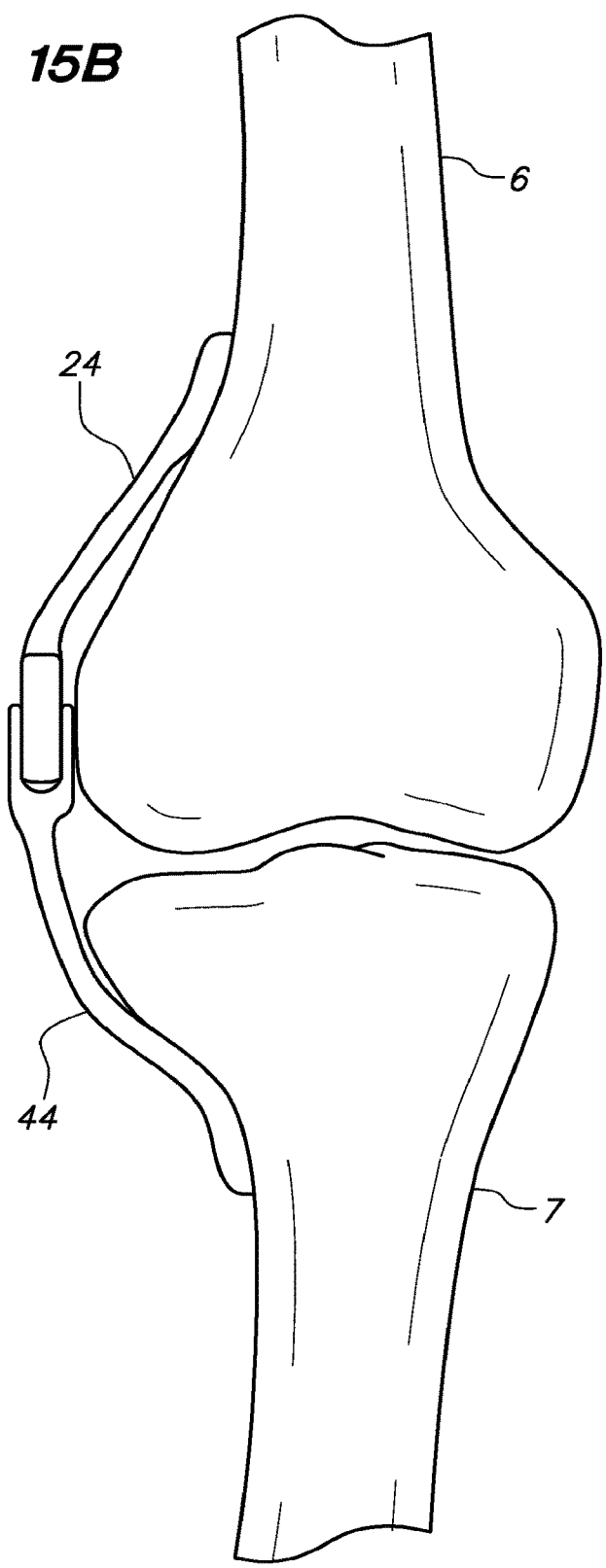

FIGS. 15A-15C illustrate the relative bending of the flex member 24 and 44 at various ranges of flexion/extension of the knee joint according to one embodiment of the present invention. In FIG. 15A, the knee is in full extension (i.e., 0 degrees flexion) and the forces applied through assembly 10 cause flex members 24 and 44 to bend (flex) outwardly in directions indicated by the arrows 8 in FIG. 15A. In this orientation, the compliance member 36 (not shown) is also deformed to absorb load.

FIG. 15B shows the knee joint in a 10 degrees of flexion orientation. In this embodiment, assembly 10 is configured to be unloaded even, at 10 degrees of flexion. Accordingly, in FIG. 15B the flex members 24 and 44 are no longer bent or bowed outwardly, like in FIG. 15A, but have returned to their resting (unbent) configurations. The compliance member 36 is also unloaded or substantially unloaded.

Likewise, in FIG. 15C, when the knee is flexed 90 degrees, the flex members 24,44 are also unflexed (unbent) and the compliance member 36 is unloaded.

Note that in FIGS. 12-15, the terminal end portions of the femur 6 and tibia 7 are depicted without surrounding tissue, for purposes of simplicity and clarity. It is noted that the bases 22 and 42 are contoured to match potential mounting surfaces of the femur and tibia.

Optionally, assembly 10 can be provided with a subcutaneous tissue barrier in the form of a sheath 58 (represented in phantom lines in FIG. 15A), preferably polytetrafluoroethylene (ePTFE), which encloses various parts of the system, particularly the joint 30, and excludes surrounding tissue. It is contemplated that the subcutaneous tissue barrier can be formed from or coated alternatively with a tissue in-growth substance or for that matter, substances which inhibit such in-growth. For example, it may be desirable that one or more sides or portions of the assembly 10 enclosed by the sheath 58 be affixed to surrounding tissue whereas it may be advantageous that other portions of the system be free to move with respect to surrounding tissue. Of course, the flex members 24, 44 and joint 30 would be left to move relative to the sheath 84. Examples of some suitable sheaths are described in U.S. patent application Ser. No. 10/113,186, which is incorporated herein by reference in it's entirety.

FIGS. 16-17 illustrate another embodiment of an assembly 10 according to the present invention, with FIG. 16 showing a side view of assembly 10 installed on the medial side of a knee joint and FIG. 17 showing a partial sectional view of assembly 10 taken along line 17-17. Like the previous embodiment, assembly 10 includes a first component 20 (in this example, first component 20 is a femoral component) and a second component 40 (in this example, second component 40 is a tibial component). The femoral component 20 is configured to be attached to a distal end portion of a patient's femur 6. The femoral component 20 includes a first base 22 that is configured to be anchored to a first hone that connects at the joint, and second component 40 includes a second base 42 that is configured to be anchored to a second bone that connects at the joint.

First component 20 includes a first flex member 24 that may be integral with first base member 22, but is preferably removably fixed thereto at 26, such as by a dovetail connection with or without locking screw, or other mechanical connection that can be locked during use, but unlocked at any such time as separation of the base 22 and flex member 24 is desired. Likewise, second component 40 includes a second flex member 44 that may be integral with second base member 42, but is preferably removably fixed thereto at 46.

The opposite ends of flex members 24 and 44 that are not fixed to base members 22 and 42 are configured to form joint 30 such that the first and second components 20, 40 are joined at joint 30. In the example shown in FIG. 16, first component 20 ends as a ring member 32 that is integral with the end of flex member 24 that is opposite the end of flex member 24 fixed to base member 22. Second component 40 ends as a shackle 34 that is pinned through ring member 32, as shown. Compliance member 36 in this embodiment, has an outside diameter that is much less than the inside diameter of ring member 32, thereby leaving space 32s within, the ring 32 that is not occupied by compliance member 36. For example, the outside diameter 36d of compliance member 36 may be about 75% or less than the inside diameter 32d of ring 32, typically less than about 50%, or even down to about 25% to about 33% of the inside diameter 32d of ring member 32. In the example shown in FIG. 17, outside diameter 36d is about 35% of inside diameter 32d.

Also, compliance member 36 has a curved outer surface profile with a radius of curvature 36r of the outer surface in a direction perpendicular to the plane of the circular shape formed by compliance member 36, in contrast to the flat outer surface profile in this dimension of the compliance member 36 of the embodiment of FIG. 12. Thus, the compliance member 36 may form a portion of a sphere, for example. Further alternatively, the member 36 in this embodiment may be formed of a non-compliant material 36n, such as rigid metal, rigid polymer, etc, as compliance can be taken up by movement of the member 36n around the race formed by the inner surface of ring member 32 in a manner as described herein. Radius of curvature 36r of the outside of the compliance member 32 is typically less than the radius of curvature 32r of the inside surface of ring 32 in a direction perpendicular to the plane of the circular shape formed by ring member 32 to facilitate relative axial rotational movements between the components 20 and 40. Note that the smaller the radius of curvature 36r is relative to radius of curvature 32r, the less resistance is provided to the relative axial rotational movements described above, but the smaller the contact surface between compliance member 36 and ring member 32, as a tradeoff. It is further noted, that when compliance member 36 comprises a compliant material, the compliant nature of the elastomer forming compliance member 36 allows it to twist, and therefore some relative axial rotations between members 20 and 40 will still be permitted even when radius of curvature 36r equals radius of curvature 32r in this case.

Figure 18:
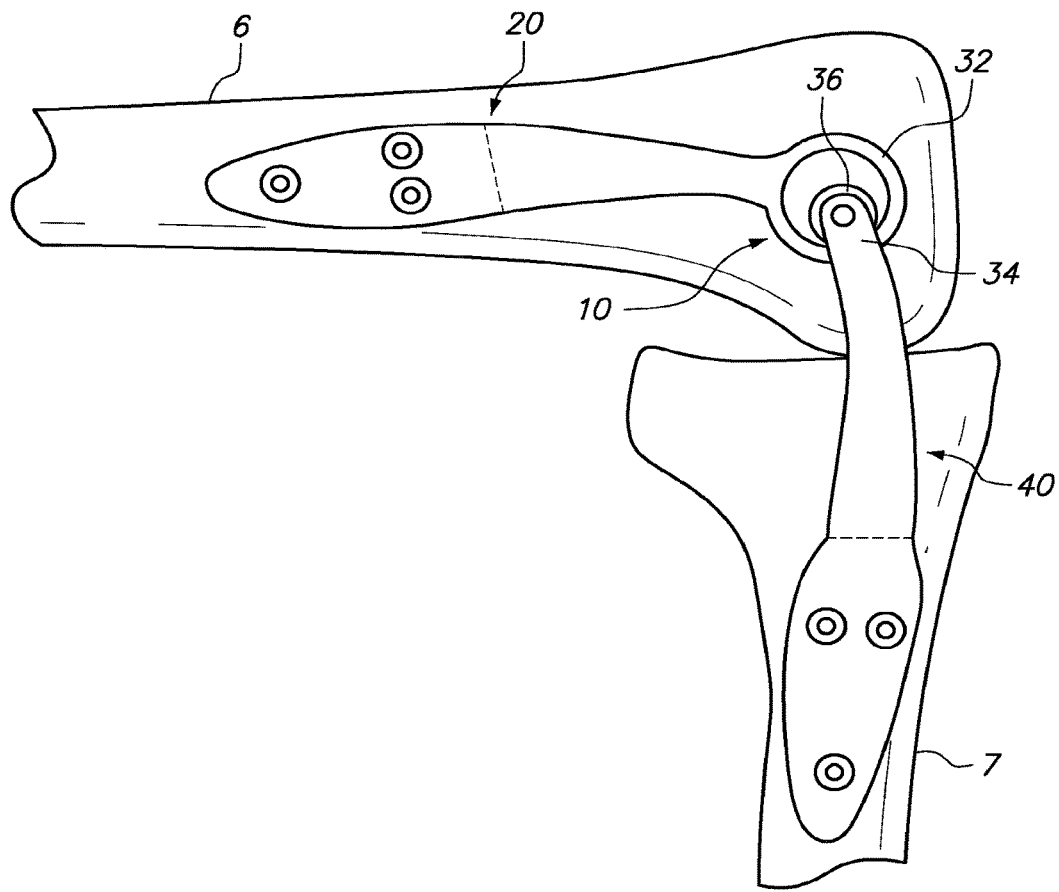
FIG. 18 illustrates the assembly of FIG. 16 when the knee joint is in flexion.
Figure 19A:
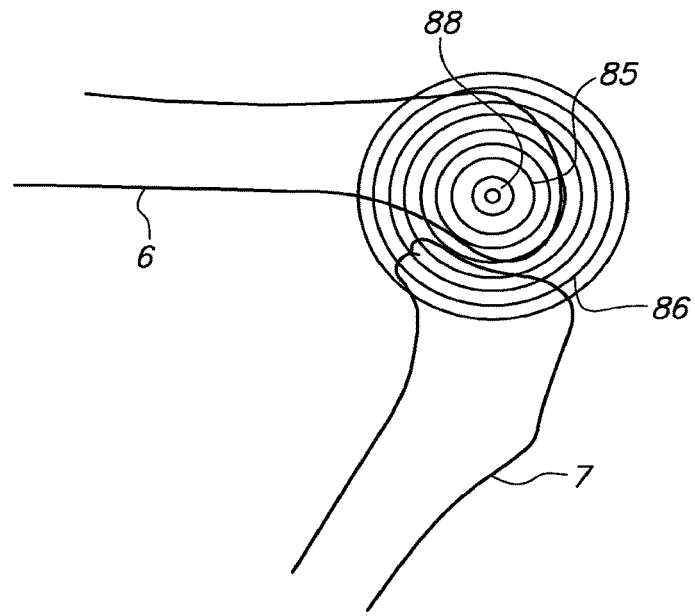
FIG. 19A illustrates imaging the knee joint using fluoroscopy according to a procedure implemented in at least one embodiment of the present invention.
Figure 19B:
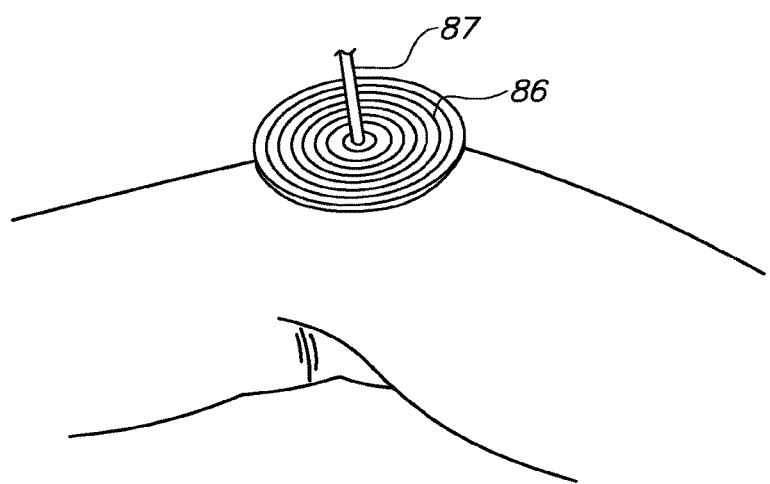
FIG. 19B illustrate use of a circle guide over the knee joint with the center thereof configured at a midpoint of the Blumensaat's line according to an embodiment of the present invention.

With the configuration of FIGS. 16-17, the position of compliance member 36 relative to ring 32, and thus the location on ring 32 where compliance member 36 contacts it (if at all) varies over the gait cycle. In extension, as illustrated in FIG. 16, compliance member 36 contacts ring 32 towards the top of the inner surface of the ring member 32, (i.e. around the 12:00 position). As the knee is flexed, the compliance member 36 moves clockwise (in the example shown in FIG. 16, but this will vary depending upon, which side of the joint that the assembly 10 is installed on), towards the 1:00, 2:00, 3:00, etc., positions until full flexion is reached, and then compliance member travels back along the inner surface of ring member 32 to the positioning shown in FIG. 16 as the knee moves from full flexion to full extension. In full flexion, or even before full flexion is reached, compliance member 36 may pull away from the inner surface of ring member 32, so that a gap exists between compliance member 36 and inner surface 32, at which time, assembly 10 does not take up any forces between the femur 6 and tibia 7. FIG. 18 illustrates a situation, where, in full flexion, compliance member 36 has pulled away from contact with the inner surface 32 of ring 32 leaving a gap therebetween.

It is noted here that joint 30, like that in FIG. 12, need not be configured to the specific arrangement shown in FIG. 16, as alternative arrangements could be provided. For example, first component 20 could be provided with shackle 34 and second component 40 could be provided with ring member 32. Further alternatively, any other structures could be provided that would form a joint between the two members 20 and 40 and perform as described above.

Flex members 24, 44 when designed for use with an adult human knee, are typically designed to flex a sufficient amount to each take up about a one to about 2.5 mm change in length thereof, typically about 1.5 mm each, for a combined compressibility of about 2 to about 5 mm, typically about 3 mm. Typically, flex members 24, 44 flex in a direction substantially normal to the direction of flexing of the anatomical joint. Thus, for example, in FIG. 13, the knee joint flexes substantially in the direction into and out of the page, while flex members flex substantially in directions aligned with the plane of the page. Assembly 10 can be configured to resist compression to force all displacement to be absorbed by the flex members 24, 44 or to absorb all forces, such as by compliance member 36, for example. Note that these are the extreme configurations over a range of configuration that can be provided. Typically, the assembly 10 is configured to provide a combination of resistance and absorption. For example, absorption of about 1 to about 2 mm of compression is typically provided by assembly 10.

Note that in FIGS. 16 and 18, the terminal end portions of the femur 6 and tibia 7 are depicted without surrounding tissue, for purposes of simplicity and clarity. It is noted that the bases 22 and 42 are contoured to match potential mounting surfaces of the femur and tibia. The bases 22, 42 can be provided in one or more shapes and size and in a variety of configurations to match the femurs and tibias of a wide variety of patients. Some additional examples of femoral and tibial base configurations are described in detail in US Patent Publication No. 2008/0275562 which is incorporated herein by reference in it's entirety.

Optionally, assembly 10 can be provided with a subcutaneous tissue barrier in the form of a sheath 58, preferably ePTFE, which encloses various parts of the system and excludes surrounding tissue as described above.

With reference now to FIGS. 19A-24, aspects of a contemplated implantation approach are described. With the anatomy of the knee joint in mind, a pre-operative or intra-operative session with the patient is conducted. By employing two-dimensional or three dimensional static or motion imaging techniques which are available, such as x-ray, MRI or CT scans, the anatomy of the interventional site is examined. A dynamic assessment can be performed to map the articulating motion of the members defining the particular joint.

The data collected during the pre-operative or intra-operative session is logged and then compared to data sets developed by the physician and/or the organization utilized to store actual patient data as well as tested theoretical data independently developed. Easily accessible and convenient to use programs or charts can be developed and employed to automate the comparison of a particular patient's condition with previously collected data. From this comparison, a specific treatment modality is selected for the patient. Moreover, an expected device (assembly 10 or portions of assembly 10, e.g., base members 22, 42) selection or multiple device selections are made from the various devices contemplated to treat the patient.

The pre-operative session, or an intra-operative session further includes the collection of three-dimensional information concerning an expected proximal attachment site (PAS) and a distal attachment site (DAS). This lends itself to the selection of the proper bases 22, 42 which may vary in shape and size and particularly in regard to their surface curvatures/conformations that are expected to conform to the bone surfaces to which they are be attached.

Once the surgical intervention date is set and as it approaches, the patient's health is continued to be closely monitored. On the day of the procedure, the patient is prepared for surgery in the conventional manner. In a particular application, spinal anesthesia or general anesthesia can be used as a step to prepare the patient.

Next, the knee or other joint being treated is imaged using fluoroscopy (See FIG. 19A) or along with three-dimensional navigational software such as that available from Stryker, Medtronic or Brainlab. The members defining the joint are placed in a full lateral position and perpendicularly to the receiver of the imaging device. The proximal joint member is then fixed using a vacuum splint/sandbag (not shown) or similarly effective device. In a preferred procedure to treat the knee joint, the Blumensaat's line 85 of the femur bone 6 is used as a landmark for locating the various components of an energy manipulation device 10 as it has been found to provide a convenient initial position marker for ultimately achieving proper rotational positioning of the device. Other referencing points can additionally be used and of course are required when treating other joints.

Accordingly, it is further contemplated that other regions can represent possible locations of a femoral rotation point on the medial chondyle. In order to select such an alternative point, the surface area of the medial chondyle is mapped to determine regions corresponding to changes in device length of a potentially implanted energy manipulation assembly 10 while the joint, is moved from full extension to full flexion. Areas of device increasing length and decreasing length can be mapped. Moreover, areas can also be identified where there is an initial device length increase then followed by a length decrease, and where there is an initial length decrease followed by increasing length. Mapping of areas of overlap between these various areas represent transitions from one region to a next. An area representing minimal displacement can also be identified. This information is then employed to identify the various points of rotation test suited for a particular energy manipulation assembly implant 10. As device/assembly 10 rotates only about joint 30 which is to be located over a location on the femur, the fixation of both bases 22 and 42 are determined by the location of placement of the center of rotation of joint 30, which is approximated as the central axis of pin 38. This is particularly important with the embodiment of FIG. 12. The embodiment of FIG. 16 can accommodate some extension throughout flexion.

In one alternative embodiment, ring member 32 may not be perfectly round. Ring member 32 operates, in conjunction with yoke 34 and members 36 and 38 to provide a force contact transmission surface over some, but not all degrees of flexion.

Furthermore, an approach to proper implant placement can involve observing changes resulting from changing the proposed location of pin 38. Trial flex members 24, 44 that are not connected by pin 38 are move through the range of motion of the anatomical joint. For example, at 90 degrees flexion, the distance between the original location of the pin 38 and the resulting location of the pin 38 at 90 degrees flexion is measured. By repeating this process, each time rearranging the pin 38 at a new location, the location of pin 38 and locations where the flex members 24, 44 will be connected to the femur and tibia, respectively (i.e., by bases 22 and 42, respectively), can be chosen based on a shift of the location of pin 38 that provided unloading during flexion, but will not shift outside of the constraints placed on the anatomical joint by the joint 30.

Alternatively as shown in FIG. 18B, a K-wire 87 can be inserted into the femur at about a midpoint along the Blumensaat's line. Preferably, the K-wire is inserted about 0.5-2 mm above and anterior to the midpoint of Blumensaat's line.

By maintaining the joint 30 over this estimated rotation point defined by the K-wire 87 and temporarily fixing bases 22 and 42 at the fixation locations on the femur 6 and tibia 7 dictated by the placement of the joint 30, while the knee joint is in full extension, the knee joint can then be manipulated through its range of motion to simulate the gait cycle and observe the elongation of the assembly 10. The assembly 10 should typically be at its most compressed when the knee joint is in full extension and then should gradually elongate over at least a portion of the gait cycle toward full flexion. The best rotation point can be determined empirically by moving the location of K-wire insertion until the actions of the assembly over the course of the gait cycle have been optimized.

Figure 20:
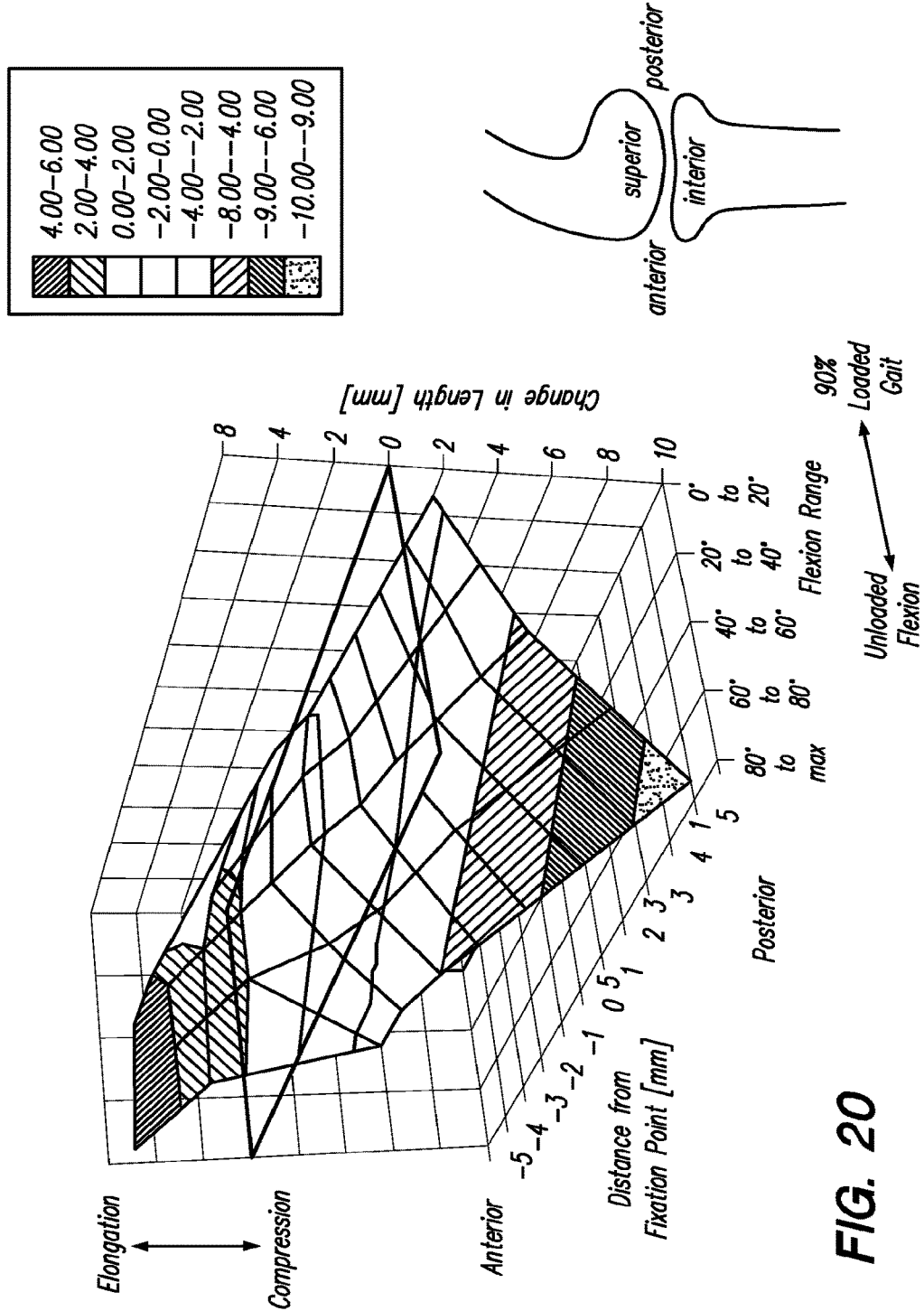
FIG. 20 is a diagrammatic view, depicting motion patterns and selected fixation points for energy manipulation devices according to an embodiment of the present invention.

In an alternative approach, a circle guide 86 is placed over the natural joint with the center thereof configured at a midpoint of the Blumensaat's line 85 (FIGS. 19A and 19B), and as described in US Patent Application Publication No. 2008/0275561 titled "Extra-Articular Implantable Mechanical Energy Absorbing Systems and implantation Method, which application is hereby incorporated herein, in its entirety, by reference thereto. As shown in FIG. 20, it has teen found that when considering device elongation and compression, along with anterior and posterior device positioning as well as flexion degrees during a patient's gait, that +/−5 mm from a center point of a Blumensaat's line can be a starting reference point At this point, it is confirmed that the tibial plateau at 90° flexion is 1-2 rings outside of an initial matching circle at 0° flexion, if the assembly 10 selected for the patient is only meant to extend during flexion. At a mid-point of the Blumensaat's line and perpendicularly thereto, the physician will then insert a rigid guide or K-wire 87 through a center guide hole 88 of the circle guide 86 that has been previously locked in place. The K-wire 87 includes a sharp terminal tip for entering bone and thus the K-wire 87 can either be drilled into the bone or tapped in by force. After the K-wire 87 has been fixed perpendicularly to the bone, the circle guide 86 is removed and the K-wire is shortened leaving approximately one inch of wire protruding through the skin. Assembly 10 may then be placed, over the K-wire 87 and the locations of fixation of bases 22 and 42 can be estimated in the manner described above, while using remote image techniques.

Figure 21:
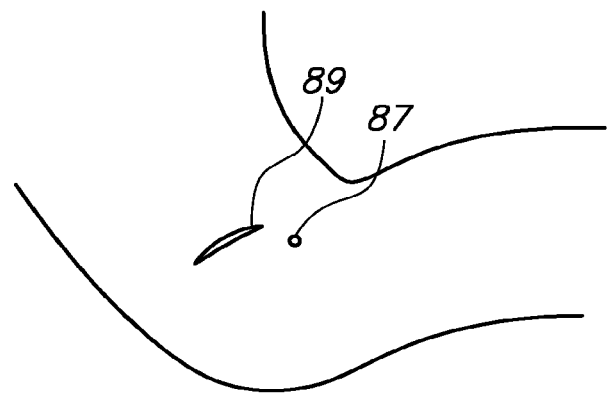
FIG. 21 illustrates a slit made superior to a K-wire placed in the femur according to an embodiment of the present invention.

With specific reference to FIG. 21, once the rotation point has been located, and fixation locations of the bases 22, 42 have been estimated, assembly 10 can be removed off of K-wire 87 and an incision 89 is made superior to the K-wire 87. Additionally, an incision. 93 is made inferior to the K-wire 87, see FIG. 24. Fascia and tissue are then manipulated to expose bone periostium in the region of anticipated base attachments to the femur 6 and tibia 7. A subcutaneous channel, is then formed either by hand or with blunt instrumentation to connect the two incisions 89, 93 and accommodate the joint 30. Alternatively, only one incision 89 or 93 can be used from winch to form a subcutaneous channel of equal length to the one described above that connect incisions 89 and 93. Further alternatively, one long incision can be formed with a length of the previously described subcutaneous channel. Further alternatively, a single small incision can be made at the center (e.g., location of K-wire 87) and a tunnel can be formed to extend superiorly and interiorly therefrom. In any case, assembly 10 is inserted either into the elongated incision, or through the subcutaneous tunnel to place the joint 30 over the rotation point having been previously determined. In instances where K-wire 87 is present joint 30 may be centered over the same. For example, pin 38 may be provided with an annulus or axially extending central through hole (not shown) configured and dimensioned to allow K-wire 87 to pass therethrough. In this case, pin 38 is slid down over K-wire 87 to temporarily fix joint 30 at the desired rotation point.

Figure 22:
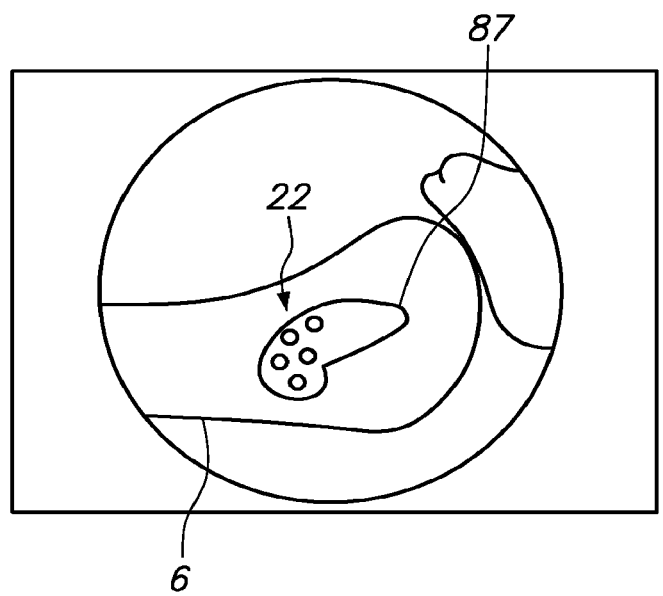
FIG. 22 illustrates visualization of a base an assembly under fluoroscopy in preparation for attaching it to the femur according to an embodiment of the present invention.
Figure 23:
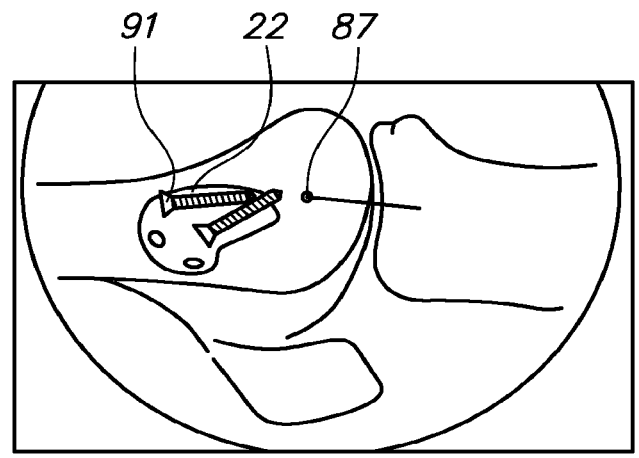
FIG. 23 illustrates fluoroscopic visualization of a base of an assembly having been attached to the femur according to an embodiment of the present invention.
Figure 24:
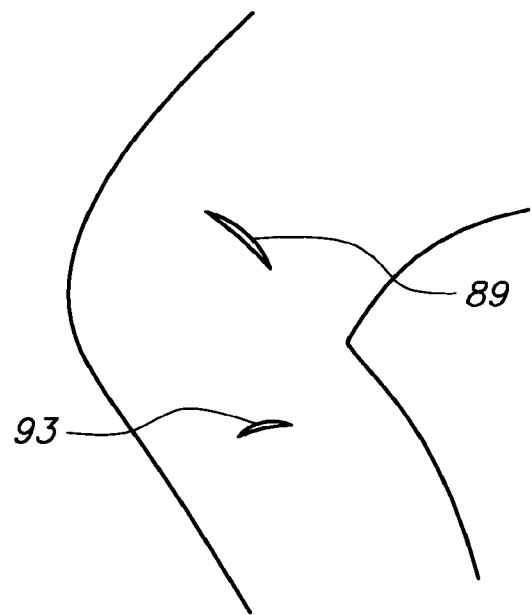
FIG. 24 illustrates slits formed superior and inferior to the anatomical joint according to an embodiment of the present invention.

The bases 22, 42 can next be fixed to the femur 6 and tibia 7 at the previous located fixation locations, the fascia, tissue and periosteum having been previously manipulated to expose the fixation locations on the bone. FIG. 22 illustrates visualization of base 22 under fluoroscopy in preparation for attaching it to the femur 6. The bases 22 and 42 are affixed to the femur 6 and tibia 7, respectively, using bone screws 91 as schematically represented in FIG. 23 and which may be accomplished under fluoroscopic visualization, for example. Prior to completely turning the screws to fix the bases 22, 42, further adjustment may be performed. Once the screws 91 have been fully torqued down to fix the positions of bases 22, 42, K-wire 87, if present, can be removed from joint 30. It is to be further recognized that various angles of insertion of the bone screws 91 can be used to aid in providing attachment support in a multitude of directions. Moreover, bi-cortical penetration of one or more of the bone screws is contemplated for certain applications.

In one approach, it is contemplated that bicortical screws can be polyaxial because their trajectory will be fixed by the bicortical purchase. Their trajectories can either diverge or converge by about 15 to 30 degrees to improve pull out strength but the exact angle is not critical so the technique can be simplified by letting them rotate in a small cone. Further, the unicortical screws can have fixed trajectories. This will increase their stability that they may lack because of the unicortical purchase. The trajectories should either converge or diverge as above but the angles will be set. It may further be desirable to use a resorbable bone void filler under the bases to eliminate gaps and prevent ingrowth of fibrous tissues. An anti back-out feature is contemplated for the screws in certain applications. Examples of anti back-out features include locking screws with heads threaded into the bases or rotating locking mechanisms on the bases which partially cover the heads of the screws.

Once the energy manipulation device assembly 10 is completely implanted, the incisions are closed and allowed to heal. Subsequent post-operative steps are taken, to verify proper placement and to accomplish any necessary adjustment. In this regard, two or three-dimensional motion imaging techniques can be used to observe effectiveness.

Further details of methods described above, as well as alternative techniques and methods for locating, orienting, positioning and implanting assembly/device 10 can be found in Application Publication No. 2009/0014016 filed Apr. 30, 2008, which application is hereby incorporated herein, in its entirety, by reference thereto.

The bone contacting surfaces of any of the bases 22, 42 described herein, can be modified to induce bone growth. Osteointegration can be obtained through mechanical interlocking or as a result of chemical loading. For example, the bone contacting surfaces may be coated with bone morphogenic protein 2 (BMP-2), hydroxy apatite (HA), titanium, cobalt chrome beads, or any other osteo-generating substance. According to one embodiment, a titanium plasma spray having a thickness of approximately 0.033 in. ±0.005 in. is applied to the inner surface 28. In another embodiment, a HA plasma spray having a thickness of approximately 35 μm±10 μm is applied alone or in combination, with the titanium plasma spray coating to facilitate osteo-integration.

Each of the embodiments described herein can incorporate or cooperate with sensing mechanisms adapted to provide loading information concerning the tissues being treated. Thus, it is contemplated that the various pressure sensing mechanisms available can be placed upon the devices of the present invention. Such sensors can be configured to provide information about the efficacy of the energy manipulating device of the present invention and whether adjustments are necessary. Similarly, sensors can be placed on anatomy to provide information regarding loads being placed on the tissues themselves.

Furthermore, it is contemplated that drugs can be delivered to the interventional site targeted for energy manipulation. In this regard, the entirety of the subject matter disclosed in U.S. Publication No. 2007/0053963 is hereby incorporated herein, by reference thereto.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

That which is claimed is:

1. An implantable assembly comprising:
   a first component configured to be attached to a first bone of a knee joint;
   a second component configured to be attached to a second bone of the knee joint;
   a rotational joint between the first and second components; and
   a compliance member comprising a flexible cylindrical member connected to the first component and a pin member positioned within the cylindrical member and connected to the second component, wherein the compliance member is configured to absorb energy transferred from the first component to the second component;
   wherein
   the second component comprises a shackle, and the pin is rotatably mounted to said shackle.

2. The implantable assembly of claim 1, wherein the pin member and the flexible cylindrical member are axially rotatable with respect to one another.

3. The implantable assembly of claim 1, wherein the first and second components each include at least one bone screw for attaching to the first and second bones.

4. The implantable assembly of claim 1, wherein the assembly is configured to both absorb and dampen energy during the gait cycle.

5. The implantable assembly of claim 1, wherein the assembly is configured to be attached to the medial side of the knee joint.

6. The implantable assembly of claim 1, wherein the assembly is configured to be implanted entirely outside of the knee joint capsule.

7. The implantable assembly of claim 1, wherein the compliance member is formed of a biocompatible elastomeric material.

8. The implantable assembly of claim 1, wherein the compliance member is configured to flex to reduce an amount of load that is applied through the natural knee joint.

9. The implantable assembly of claim 1, wherein the compliance member is configured to deform and twist to accommodate relative axial rotation between the first and second components.

10. The implantable assembly of claim 1, wherein the assembly is configured to relieve load on a side of the knee joint to which said assembly is attached.

11. The implantable assembly of claim 1, wherein the assembly is configured to deflect, bend or twist to absorb energy that is normally applied through the natural knee joint without the use of a metallic spring.

\* \* \* \* \*